(12) United States Patent
Eldridge

(10) Patent No.: US 7,604,978 B2
(45) Date of Patent: Oct. 20, 2009

(54) INHIBITION OF BIOFILM FORMATION

(75) Inventor: Gary R. Eldridge, Encinitas, CA (US)

(73) Assignee: Sequoia Sciences, Inc., St. Louis, MO (US)

( * ) Notice: Subject to any disclaimer, the term of this patent is extended or adjusted under 35 U.S.C. 154(b) by 0 days.

(21) Appl. No.: 11/085,279

(22) Filed: Mar. 21, 2005

(65) Prior Publication Data

US 2006/0014290 A1    Jan. 19, 2006

Related U.S. Application Data

(60) Provisional application No. 60/587,680, filed on Jul. 14, 2004, provisional application No. 60/609,763, filed on Sep. 14, 2004.

(51) Int. Cl.
*C12N 1/38* (2006.01)
*C12N 1/20* (2006.01)

(52) U.S. Cl. ............... 435/244; 435/252.1; 435/252.8; 435/253.3

(58) Field of Classification Search ............... None
See application file for complete search history.

(56) References Cited

U.S. PATENT DOCUMENTS

| | | |
|---|---|---|
| 3,996,132 A | 12/1976 | Mateos et al. |
| 4,606,911 A | 8/1986 | Hayashi et al. |
| 4,897,268 A | 1/1990 | Tice et al. |
| 4,929,365 A | 5/1990 | Clark et al. |
| 5,075,109 A | 12/1991 | Tice et al. |
| 5,312,813 A | 5/1994 | Costerton et al. |
| 5,462,644 A | 10/1995 | Woodson |
| 5,789,239 A | 8/1998 | Eyers et al. |
| 5,834,437 A | 11/1998 | Jew et al. |
| 5,882,916 A | 3/1999 | Wiersma et al. |
| 5,906,825 A | 5/1999 | Seabrook et al. |
| 5,985,601 A | 11/1999 | Nl et al. |
| 6,080,323 A | 6/2000 | Yu et al. |
| 6,264,926 B1 | 7/2001 | Farooqi et al. |
| 6,267,897 B1 | 7/2001 | Robertson et al. |
| 6,267,979 B1 | 7/2001 | Raad et al. |
| 6,369,101 B1 | 4/2002 | Carlson |
| 6,395,189 B1 | 5/2002 | Fabri et al. |
| 6,399,115 B2 | 6/2002 | Revel |
| 6,410,256 B1 | 6/2002 | Ceri et al. |
| 6,423,219 B1 | 7/2002 | Chandler |
| 6,455,031 B1 | 9/2002 | Davies et al. |
| 6,468,549 B1 | 10/2002 | Dupuis et al. |
| 6,498,862 B1 | 12/2002 | Pierson et al. |
| 6,555,055 B1 | 4/2003 | Cisar et al. |
| 6,585,961 B1 | 7/2003 | Stockel |
| 6,596,505 B2 | 7/2003 | Ceri et al. |
| 6,669,929 B1 | 12/2003 | Boyd et al. |
| 6,762,160 B2 | 7/2004 | Barbeau et al. |
| 6,946,124 B2 | 9/2005 | Arnaud-Sebillotte et al. |
| 2002/0037260 A1 | 3/2002 | Budney et al. |
| 2003/0225126 A1 | 12/2003 | Markham et al. |
| 2004/0033548 A1 | 2/2004 | Bassler et al. |
| 2004/0033549 A1 | 2/2004 | Greenberg et al. |
| 2004/0136924 A1 | 7/2004 | Boyd et al. |
| 2005/0137259 A1 | 6/2005 | Matsuyama et al. |
| 2005/0143428 A1 | 6/2005 | Dunkel et al. |
| 2006/0014285 A1 | 1/2006 | Eldridge et al. |
| 2006/0014290 A1 | 1/2006 | Eldridge |
| 2006/0228384 A1 | 10/2006 | Eldridge |
| 2006/0264411 A1 | 11/2006 | Eldridge |
| 2007/0014739 A1 | 1/2007 | Eldridge |
| 2008/0145322 A1 | 6/2008 | Eldridge |

FOREIGN PATENT DOCUMENTS

| | | |
|---|---|---|
| WO | WO 98/08091 A1 | 2/1998 |
| WO | WO 98/08091 A1 | 2/1998 |
| WO | WO 2006/010147 A2 | 1/2006 |
| WO | WO 2006/019881 A2 | 2/2006 |
| WO | WO 2006/019926 A2 | 2/2006 |
| WO | WO 2006/031943 A1 | 3/2006 |
| WO | WO 2006/102255 A1 | 9/2006 |

OTHER PUBLICATIONS

Delic-Attree et al., Mol. Microbiol., 1997, 24(6), 1275-1284.*
Rakonjac et al., Mol. Gen. Genet., 1991, 228, 307-311.*
Schuhly et al., Planta Medica, 1999, 65, 740-743.*
Chambers 21st Century Dictionary, Chambers Harrap Publishers Limited 2001, Retrieved Jul. 7, 2008, from http://www.credoreference.com/entry/1215201.*
International Search Report for PCT/US2006/010088, published by the International Bureau of WIPO on Sep. 28, 2006 under WO 2006/102255 A1.
Anderson et al., Intracellular Bacterial Biofilm-Like Pods in Urinary Tract Infections,www.sciencemag.org, Jul. 4, 2003, pp. 105-107.
Borum, P. R. and Monty, K. J., Regulatory Mutants and Control of Cysteine Biosynthetic Enzymes in *Salmonella typhimurium*; Journal of Bacteriology, Jan. 1976, p. 94-101, vol. 125, No. 1, U.S.A.
Ding, H. and Demple, B., Thiol-Mediated Disassembly and Reassembly of [2Fe-2S] Clusters in the Redox-Regulated Transcription Factor SoxR; American Chemical Society, 1998, p. 17280-17286, vol. 37, published on Web Nov. 19, 1998.
Gallardo-Madueno, R., et al., In Vivo Transcription of *nrdAB* Operon and of *grxA* and *fpg* Genes I Triggered in *Escherichia coli* Lacking both Thioredoxin and Glutaredoxin 1 or Thioredoxin and Glutathione, Respectively; Journal of Biological Chemistry, Jul. 17, 1998, p. 18382-18388, vol. 273, No. 29, The American Society for Biochemistry and Molecular Biology, Inc., U.S.A.

(Continued)

*Primary Examiner*—Nancy Vogel
(74) *Attorney, Agent, or Firm*—Gallop, Johnson & Neuman, LC; Kenneth Solomon; Don V. Kelly

(57) ABSTRACT

The present invention relates to compositions and methods for reducing or inhibiting biofilm comprising modulating expression of a cysB gene in a cell. The invention also provides methods for modulating the expression of a cysB, cysD, cysI, cysJ, cysK, and ybiK. The invention further provides methods for identifying gene(s) involved in biofilm formation and for identifying biofilm inhibitors.

15 Claims, 9 Drawing Sheets

OTHER PUBLICATIONS

Hogema, B. M., et al., Inducer exclusion in *Escherichia coli* by non-PTS substrates: the role of the PEP to pyruvate ratio in determining the phosphorylation state of enzyme IIA$^{Glc}$, Molecular Microbiology, 1998, p. 487-498, vol. 30(3), Blackwell Science Ltd.

Jackson, D. W. et al., Biofilm Formation and Dispersal under the Influence of the Global Regulator CsrA of *Escherichia coli*, Journal of Bacteriology, Jan. 2002, p. 290-301, vol. 184, No. 1.

Kiley, P. J. and Beinert, H., the role of Fe-S proteins in sensing and regulation in bacteria, Current Opinion in Microbiology, 2003, p. 181-185, vol. 6, www.currentopinion.com.

Miranda-Vizuete, A. et al., The Levels of Ribonucleotide Reductase, Thioredoxin, Glutaredoxin 1, and GSH Are Balanced in *Escherichia coli* K12, The Journal of Biological Chemistry, Aug. 9, 1996, p. 19099-19103, vol. 271, No. 32, The American Society for Biochemistry and Molecular Biology, Inc., U.S.A.

Olofsson, A-C., et al., N-Acetyl-L-Cysteine Affects Growth, Extracellular Polysaccharide Production, and Bacterial biofilm Formation on Solid Surfaces, Applied and Environmental Microbiology, Aug. 2003, p. 4814-4822, vol. 69, No. 8, American Society for Microbiology.

Perez-Giraldo, C. et al., Influence of N-acetylcysteine on the formation of biofilm by *Staphylococcus epidermidis*, Journal of Antimicrobial Chemotherapy, 1997, p. 643-646, vol. 39, The British Society for Antimicrobial Chemotherapy.

Prieto-Alamo, M-J. et al., Transcriptional Regulation of Glutaredoxin and Thioredoxin Pathways and Related Enzymes in Response to Oxidative Stress, May 5, 2000, p. 13398-13405, vol. 275, No. 18, The American Society for Biochemistry and Molecular Biology, Inc., U.S.A.

Rashid, M. H. et al., Polyphosphate kinase is essential for biofilm development, quorum sensing, and virulence of *Pseudomonas aeruginosa*; Proc. Natl. Acad. Sci. 10.1073/pnas.170283397, Aug. 15, 2000, p. 9636-9641, vol. 97, No. 17.

Singh, P. K. et al., A component of innate immunity prevents bacterial biofilm development; Nature, May 30, 2002, p. 552-555, vol. 417, Nature Publishing Group.

Tran, Q. H., et al. Role of glutathione in the formation of the active form of the oxygen sensor FNR ([4Fe-4S]-FNR) and in control of FNR function, Eur. J. Biochem., 2000, p. 4817-4824, vol. 267.

Vergauwen, B., et al., Exogenous Glutathione Completes the Defense against Oxidative Stress in *Haemophilus influenzae*, Journal of Bacteriology, Mar. 2003, p. 1572-1581, vol. 185, No. 5, American Society for Microbiology.

International Search Report for PCT/US2005/24946 (WO 2006/010147), Publication Date Jan. 26, 2006, Eldridge, Gary R.

International Search Report for PCT/US2005/25016 (WO/2006/019926 A2), Publication Date Feb. 23, 2006, Eldridge, Gary R.

International Search Report for PCT/US2005/032874 (WO 2006/03943), Publication Date filed Mar. 23, 2006, Eldridge, Gary R.

International Search Report for PCT/US2005/24945 (No WO publication), Publication Date Apr. 18, 2006, Eldridge, Gary R.

Adler and Epstein, Phosphotransferase-System Enzymes as Chemoreceptors for Certain Sugars in *Escherichia coli* Chemotaxis, Proc. Nat. Acad. Sci. USA, Jul. 1974, 71(7): 2895-2899.

Akamatsu, H. et al., the inhibition of free radical generation by human neutrophils through the synergistic effects of metronidazole with palmitoleic acid: a possible mechanism of action of metronidazole in rosacea and acne, Archives of Dermatological Research, 1990, 282: 449-454.

Ando, E. et al., Biofilm Formation Among Methicillin-Resistant *Staphylococcus aureus* Isolates from Patients with Urinary Tract Infection, Acta Med. Okayama, 2004, 58(4): 207-214.

Arevalo-Ferro, C. et al., Biofilm formation of *Pseudomonas putida* IsoF: the role of quorum sensing as assessed by proteomics, Systematic and Aplplied Microbiology, 2005, 28: 87-114.

Bannon, C. D. et al, Chlorination of Olean-12-Enes, Database Accession No. 1976:44437 Abstract & Australian Journal of Chemistry, 1976, pp. 2649-2654, vol. 28, No. 12.

Begum, S. et al, Chemical Constituents From the Leaves of Psidium Guajava, Database Accession No. 2004:177767 Abstract & Natural Product Research, 2004, pp. 135-140, vol. 18, No. 2.

Bellesta-Acosta, M. C. et al., A New 24-nor-Oleanase Triterpenoid from *Salvia carduacea*, J. Nat. Prod., 2002, 65: 1513-1515.

Boddicker, J. D. et al., Differential binding to and biofilm formation on, HEp-2 cells by *Salmonella enterica* Serovar Typhimurium is dependent upon allelic variation in the *fimH* gene of the *fim* gene cluster, Molecular Microbiology, 2002, 45(5): 1255-1265.

Bowden et al, Abstract & Database Crossfire Beilstein, Beilstein Institut zur Forderung der Chemischen Wissenschaften, Frankfurt am Main, DE, 1975, pp. 91-103, Database Accession No. BRN 2189905, Australian J. Chem., vol. 28.

Brieskorn, C. H. et al, and Eschelbach Glykamine Von ORsol—Und 18Beta-Glycyrrhetinsaure, Archiv Der Pharmazie, VCH Verlagsgesellschaft MBH, Weinheim, DE, Sep. 1, 1979, pp. 752-762, vol. 312, No. 9.

Burkhart, Craig N. et al., Microbiology's principle of biofilms as a major factor in the pathogenesis of acne vulgaris, International J. of Dermatology, 2003, 42: 925-927.

Centers for Disease Control and Prevention, Update: Investigation of Bioterrorism-Related Anthrax and Interim Guidelines for Exposure Management and Antimicrobial Therapy, Oct. 26, 2001, MMWR 2001, 50 (42): 909-919.

Centers for Disease Control and Prevention, Guidelines for the Prevention of Intravascular Catheter-Related Infections, MMWR, 2002, 51: No. RR-10.

Coldren, C. et al., Gene Expression Changes in the Human Fibroblast Induced by *Centella asiatica* Triterpenoids, Planta Med., 2003, 69: 725-732.

Conley, J. et al., Biofilm Formation by Group A Streptococci: Is There a Relationship with Treatment Failure?, J. Clin. Microbiol., Sep. 2003, 41(9): 4043-4048.

Corey E. J. and Lee, J.; Enantioselective Total Synthesis of Oleanolic Acid, Erythrodiol, β-Amyrin, and Other Pentacyclic Triterpenes from a Common Intermediate, J. Am. Chem. Soc., 1993, 115: 8873-8874.

Cortés, G. et al., Role of Lung Epithelial Cells in Defense against *Klebsiella pneumoniae* Pneumonia, Infect. and Immun., Mar. 2002, 70(3): 1075-1080.

Cossart P. and Sansonetti, P.J., Bacterial Invasion: The Paradigms of Enteroinvasive Pathogens, Science, Apr. 9, 2004, 304: 242-248.

Costerton, J. W. et al., Bacterial Biofilms: A Common Cause of Persistent Infections, Science, May 21, 1999, 284: 1318-1322.

Cremin P.A. and Zeng, L., High-Throughput Analysis of Natural Product Compound Libraries by Parallel LC-MS Evaporative Light Scattering Detection, Anal. Chem., Nov. 1, 2002, 74(21): 5492-5500.

Drefahl, G. and Huneck, S., Ueber Reduktionsprodukte Verschiedener Triterpenoxime Und Triterpensaeureamide, Chemische Berichte, Verlag Chemie GMBH Weinheim, DE, 1960, pp. 1967-1975.

Drehfahl, Huneck, & Abstract Database Crossfire Beilstein, Beilstein Institut zur Forderung der Chemischen Wissenschaften, Frankfurt am Main, DE, Database Accession No. BRN 2824441, 4114508, 2825723, Chem. Ber., 1961, pp. 1145-1150, vol. 94.

Edwards, R. and Harding, K.G., Bacteria and wound healing, Curr. Opin. Infect. Dis., 2004, 17: 91-96.

Eldridge, G. et al., High-throughput method for the production and analysis of large natural product libraries for drug discovery, Anal. Chem., 2002, 74(16): 3963-3971.

Elsinghorst, Eric A., Measurement of Invasion by Gentamicin Resistance, Methods in Enzymology, 1994, 236: 405-420.

Farina, C. et al., Synthesis and Anti-Ulcer Activity of New Derivatives of Glycyrrhetic, Oleanolic and Ursolic Acids, II Farmaco, 1998, 53: 22-32.

Finlay B.B. and Cossart, P., Exploitation of Mammalian Host Cell Functions by Bacterial Pathogens, Science, May 2, 1997, 276: 718-725.

Fried et al, J. Structure-Activity Relationship in the Field of Antibacterial Steroid Acid, J. Med. Chem., 1965, pp. 279-282, vol. 8, No. 3.

Frimodt-Moller, Niels, Correlation Between Pharmacokinetic/Pharmacodynamic Parameters and Efficacy for Antibiotics in the Treatment of Urinary Tract Infection, International Journal of Antimicrobial Agents, 2002, 19: 546-553.

Gao, Ze-Li et al., Effect of Sea buckthorn on liver fibrosis: A clinical study, World J. Gastroenterol., 2003, 9(7):1615-1617.

Garcia-Granados, A. Epoxides, Cyclic Sulfites, and Sulfate from Natural Pentacyclic Triterpenoids: Theoretical Calculations and Chemical Transformations, J. Org. Chem., 2003, pp. 4833-4844, vol. 68, No. 12.

Greiner, L. et al., Biofilm Formation by *Neisseria gonorrhoeae*, Infect. and Immun., Apr. 2005, 73(4): 1964-1970.

Greiner, L. C. et al., Nontypeable *Haemophilus influenzae* Strain 2019 Produces a Biofilm Containing N-Acetylneuraminic Acid That May Mimic Sialylated O-Linked Glycans, Infect. and Immun., Jul. 2004, 72(7): 4249-4260.

Hanna, H.A. et al., Antibiotic-Impregnated Catheters Associated with Significant Decrease in Nosocomial and Multidrug-Resistant Bacteremias in Critically Ill Patients, Chest, 2003, 124(3): 1030-1038.

Harrison-Balestra, C. et al., A Wound-isolated *Pseudomonas aeruginosa* Grows a Biofilm in Vitro Within 10 Hours and Is Visualized by Light Microscopy, Dermatol Surg, 2003, 29: 631-635.

Hichri, Faycal et al, Antibacterial Activities of a Few Prepared Derivatives of Oleanolic Acid and of Other Natural Triterpenic Compounds; Comptes Rendus Chimie, 2003, pp. 473-483, vol. 6, No. 4.

Honda, T. et al., Design and Synthesis of 2-Cyano-3,12-Dioxoolean-1,9-Dien-28-Oic Acid, a Novel and Highly Active Inhibitor of Nitric Oxide Production in Mouse Macrophages, Bioorganic & Medicinal Chemistry Letters, 1998, 8: 2711-2714.

Honda, T. et al., New Enone Derivatives of Oleanolic Acid and Ursolic Acid as Inhibitors of Nitric Oxide Production in Mouse Macrophages, Bioorganic & Medicinal Chemistry Letters, 1997, 7(13): 1623-1628.

Howell-Jones, R. S. et al., A review of the microbiology, antibiotic usage and resistance in chronic skin wounds, J. Antimicrob. Ther., Jan. 2005, 55(2): 143-149.

Hsu, H. et al., Methods of Decocting and Administering Herbal Drugs, and 382. Centellae Herba, Oriental Materia Medica: A Concise Guide, Oriental Healing Arts Institute, 1986, 39-40 and 443-444.

Huang, A. X. et al., An Exceptionally Short and Simple Enantioselective Total Synthesis of Pentacyclic Triterpenes of the β-Amyrin Family, J. Am. Chem. Soc., 1999, 121: 9999-10003.

Ikuta, A. et al., Ursane- and Oleannane-Type Triterpenes from *Temstroemia gymnanthera* Callus Tissues, J. Nat. Prod., 2003, 66: 1051-1054.

Isobe, T. et al, Studies on the Constituents of Leucoseptrum Stellipillum, STN Database Accession No. 1989:404261 Abstract & Natural Product Research 1989, pp. 175-178, vol. 109, No. 3.

Jain, S.M., Atal, C. K., & Abstract Database Crossfire Beilstein, Beilstein Institut zur Forderung der Chemischen Wissenschaften, Frankfurt am Main, DE, Database Accession No. BRN, 5692755, 5775629, Indian J. Chem., 1986, pp. 427-428, Sect. B, vol. 25.

Jarrett, C.O. et al., Transmission of *Yersinia pestis* from an Infectious Biofilm in the Flea Vector, JID, Aug. 15, 2004, 190: 783-792.

Jones, S.M., et al., Effect of vancomycin and rifampicin on methicillin-resistant *Staphylococcus aureus* biofilms, Lancet, 2001, 357: 40-41.

Kartnig, T., Clinical Applications of *Centella asiatica* (L.) Urb., Herbs, Spices and Medicinal Plants, Orxy Press, Arizona, USA, 1998, 3: 145-173.

Kaufman, P. B. et al., Phytochemicals: The Chemical Components of Plants and Bioseparation of Compounds, Chapters 1 and 7, Natural Products from Plants, CRC Press LLC, Boca Raton, USA, 1999, 1-36 and 207-240.

Konoike, T. et al. Synthesis of [2-$^{13}$C]-Oleanolic Acid and [2-$^{13}$C]-Myricerone, Tetrahedron, 1999, 55: 14901-14914.

Landa, A. S. et al., Efficacy of Ophthalmic Solutions to Detach Adhering *Pseudomonas aeruginosa* from Contact Lenses, 1998, Cornea 17(3): 293-300.

Lavender, H. F. et al., Biofilm Formation In Vitro and Virulence In Vivo of Mutants of *Klebsiella pneumonia*, Infect. and Immun., Aug. 2004, 72(8): 4888-4890.

Leroy-Dudal, J. et al., Role of avβ5 integrins and vitronectin in *Pseudomonas aeruginosa* PAK Interaction with A549 respiratory cells, Microbes and Infection, 2004, 6: 875-881.

Li, Yung-Hua, et al., Natural Genetic Transformation of *Streptococcus mutans* Growing in Biofilms, J. Bacteriol., Feb. 2001, 183(3): 897-908.

Liaw, Shwu-Jen., et al., Modulation of swarming and virulence by fatty acids through the RsbA Protein in *Proteus mirabilis*, Infect. Immun., Dec. 2004, 72(12): 6836-6845.

Linde, H. Zur Synthese Einiger Stickstoffhaltiger Oleanol- und Ursolsaurederivate, Arch. Pharm., 1979, pp. 832-837, vol. 312.

Lipsky, Benjamin A., Medical Treatment of Diabetic Foot Infections, CID, 2004, 39 (Suppl 2): S104-S114.

Little, C. S. et al., Age Alterations in Extent and Severity of Experimental Intranasal Infection with *Chlamydophila pneumoniae* in BALB/c Mice, Infection and Immunity, Mar. 2005, 73(3): 1723-1734.

Ma, Chao-Mei et al, Chemical Modification of Oleanene Type Triterpenes and Their Inhibitory Activity Against HIV—1Protease Dimerization, Chemical & Pharmaceutical Bulletin, 2000, pp. 1681-1688, vol. 48, No. 11.

Maki, D. G. et al., Prevention of Central Venous Catheter-Related Bloodstream Infection by Use of an Antiseptic-Impregnated Catheter, Ann. Int. Med., 1997, 127(4): 257-266.

Martinez, J. J. et al., Type 1 pilus-mediated bacterial invasion of bladder epithelial cells, The EMBO Journal, 2000, 19(12): 2803-2812.

Martinez, J. J. and Hultgren, S.J., Requirement of Rho-family GTPases in the invasion of Type 1-piliated uropathogenic *Escherichia coli*, Cellular Microbiology, 2002, 4(1): 19-28.

McLaughlin-Borlace, L. et al., Bacterial biofilm on contact lenses and in lens storage cases in wearers with microbial keratitis, J. of Applied Microbiology, 1998, 84: 827-838.

Menzies, B. E., The role of fibronectin binding proteins in the pathogenesis of *Staphylococcus aureus* infections, Curr. Opin. Infect. Dis., 2003, 16: 225-229.

Mi, Y. et al., Total Synthesis of (+)-α-Onocerin in Four Steps via Four-Component Coupling and Tetracyclization Steps, J. Am. Chem. Soc., 2002, 124: 11290-11291.

Mulvey, M. A. et al., Induction and Evasion of Host Defenses by Type 1-Piliated Uropathogenic *Escherichia coli*, Science, Nov. 20, 1998, 282: 1494-1497.

Murphy, K. and Campellone, K.G., Lambda Red-mediated recombinogenic engineering of enterohemorrhagic and enteropathogenic *E. coli*, BMC Molecular Biology, 2003, 4: 1-12.

Nishimura, K. et al., Activity-Guided Isolation of Triterpenoid Acyl CoA Cholesteryl Acyl Transferase (ACAT) Inhibitors from *Ilex kudincha*, J. Nat. Prod., 1999, 62: 1061-1064.

Nociari, M. M. et al., A novel one-step, highly sensitive fluorometric assay to evaluate cell-mediated cytotoxicity, J. Immunol. Met., 1998, 213: 157-167.

Ojinnaka, C. M. et al, The Chemical Constituents of Musanga Cecropioides, Database Accession No. 1985:419849 Abstract & Journal of Natural Products, 1985, p. 337, vol. 48, No. 2.

Osawa, K. et al, Antibacterial and Antihemolytic Activity of Triterpenes and .beta.-Sitosterol Isolated From Chinese Quince (Chaenomeles Sinensls), Database CA 'Online! Chemical Abstracts Service, Columbus, Ohio, US, STN Database accession No. 1997:741679 abstract & Natural Medicines, 1997, pp. 365-367, Tokyo.

Pendland, S. L. et al., In vitro synergy testing of levofloxacin, ofloxacin, and ciprofloxacin in combination with aztreonam, ceftazidime, or piperacillin against *Pseudomonas aeruginosa*. Diag. Micro. Inf. Dis., 2002, 42: 75-78.

Pirzada, O. M., et al., Improved lung function and body mass index associated with long-term use of Macrolide antibiotics, J. Cystic Fibrosis, 2003, 2: 69-71.

Price, L. B., et al., In vitro selection and characterization of *Bacillus anthracis* mutants with high-level resistance to ciprofloxacin, Antimicrob. Agents Chemother., 2003, 47(7): 2362-2365.

Raad, I. et al., Central Venous Catheters Coated with Minocycline and Rifampin for the Prevention of Catheter-Related Colonization and Bloodstream Infections, Ann. Int. Med., 1997, 127(4): 267-274.
Ramage, G. et al., Formation of *Propionibacterium acnes* biofilms on orthopaedic biomaterials and their susceptibility to antimicrobials, Biomaterials, 2003, 24: 3221-3227.
Ramsey, B. W. et al., Intermittent Administration of Inhaled Tobramycin in Patients with Cystic Fibrosis, New England J. Medicine, 1999, 340(1): 23-30.

Ren, D. et al, Differential Gene Expression for Investigation of *Escherichia coli* Biofilm Inhibition by Plant Extract Ursolic Acid, Applied and Environmental Microbiology, Jul. 2005, pp. 4022-4034, vol. 71, No. 7.

Russo, T.A. and Johnson, J.R., Medical and economic impact of extraintestinal infections due to *Escherichia coli*: focus on an increasingly important endemic problem, Microbes and Infection, 2003, 5: 449-456.

Saiman, L., The use of macrolide antibiotics in patients with cystic fibrosis, Curr. Opin. Pulm. Med., 2004, 10: 515-523.

Sauer, K. and Camper, A.K., Characterization of Phenotypic Changes in *Pseudomonas putida* in Response to Surface-Associated Growth, J. Bacteriol., Nov. 2001, 183(22): 6579-6589.

Schwab, U. E. et al., Role of Actin Filament Network in *Burkholderia multivorans* Invasion in Well-Differentiated Human Airway Epithelia, Infect. and Immun., Nov. 2003, 71(11): 6607-6609.

Slack, J. M., Stem Cells in Epithelial Tissues, (Review) Science, 2000, 287(25): 1431-1433.

Sturgill, G. et al., Role of CysE in Production of an Extracellular Signaling Molecule in *Providencia stuartii* and *Exchericia coli*: Loss *cysE* Enhances Biofilm Formation *Escherichia coli*, J. Bacteriol., Nov. 2004, 186(22): 7610-7617.

Takai, T. et al., Effects of temperature and volatile fatty acids on nitrification-denitrification activity in small-scale anaerobic-aerobic recirculation biofilm process, Water Sci. Technol., 1997, 35(6): 101-108.

Takechi, M. et al, "Structure—Activity Relationships of Synthetic Methyl Ursolate Glycosides", Phytochemistry, 1993, pp. 675-677, vol. 34, No. 3.

Tamura, Y. et al, Antimicrobial Activities of Saponins of Pericarps of Sapindus Mukurossi on Dermatophytes, STN Database Accession No. 2001:412378 Abstract & Natural Medicines, 2001, pp. 11-16, vol. 55, No. 1, Tokyo, Japan.

Utaisincharoen, P. et al., *Burkholderia pseudomallei* invasion and activation of epithelial cells requires activation of p38 mitogen-activated protein kinase, Microbial Pathgenesis, 2005, 38: 107-112.

Veeh, R. H. et al., Detection of *Staphylococcus aureus* Biofilm on Tampons and Menses Components, JID, Aug. 15, 2003, 188: 519-530.

Wang, M. et al, Studies on Chemical Constituents From Root of Rubus, STN Database Accession No. 2003:597250 Abstract & Zhongcaoyao, 2003, pp. 295-297, vol. 34, No. 4.

Wein, L.M., et al., Emergency response to an anthrax attack, PNAS, Apr. 1, 2003, 100(7): 4346-4351.

Wille, J. J. et al., Palmitoleic Acid Isomer (C16:1Δ6) in Human Skin Sebum Is Effective against Gram-Positive Bacteria, Skin Pharmacol. Appl. Skin Physiol., 2003, 16: 176-187.

Wrzeciono et al, Abstract & Database Crossfire Beilstein, Beilstein Institut zur Forderung der Chemischen Wissenschaften, Frankfurt am Main, DE, Database Accession No. BRN 3041373, 3040548, 3040547, 3040424, 2923199, Rocz. Chem., 1973, p. 955, 956, 960, 961, vol. 47.

Xie, H. et al., Intergeneric Communication in Dental Plaque Biofilms (Notes), J. Bacteriol., Dec. 2000, 182(24): 7067-7069.

Yang, B. et al., Effects of dietary supplementation with sea buckthorn (*Hippophae rhamnoides*) seed and pulp oils on atopic dermatitis, J. Nutr. Bichem., 1999, 10: 622-630.

Yoshida, M. et al., Antiproliferative Constituents from Umbelliferae Plants VII. [1)] Active Triterpenes and Rosmarinic Acid from *Centella asiatica*, Biol. Pharm. Bull., 2005, 28(1): 173-175.

Product Brochure by Indena® at www.indena.it entitled, "Gentella Asiatica Selected Triterpenes: A Highly Standardized Natural Remedy for the Maintenance of an Healthy Venous System".

Elvers, K. and Lappin-Scott, H., Biofilms and Biofouling Encyclopedia of Microbiology, vol. 1, , 2nd ed., pp. 478-485, Academic Press, San Diego, CA.

Justice, S. et al., Differentiation and developmental pathways of uropathogenic *Escherichia coli* in urinary tract pathogenesis, PNAS, Feb. 3, 2004, 101(5): 1333-1338.

Ren, D. et al., Stationary-Phase Quorum-Sensing Signals Affect Autoinducer-2 and Gene Expression in *Escherichia coli*, Applied and Environmental Microbiology, Apr. 2004, 70(4): 2038-2043.

Sauer, K. et al., Characterization of Nutrient-Induced Dispersion in *Pseudomonas aeruginosa* PA01 Biofilm, Journal of Bacteriology, Nov. 2004, 186(21): 7312-7326.

Byrne, C., et al., DNA Sequences of the *cysK* Regions of *Salmonella typhimurium* and *Escherichia coli* and Linkage of the *cysK* Regions to *ptsH*, Journal of Bacteriology, Jul. 1988, 170(7): 3150-3157.

Verschueren, K., et al., Crystallization of full-length *CysB* of *Klebsiella aerogenes*, a LysR-type transcriptional regulator, Acta Cryst., 2001, D57: 260-262.

Pratt, L. and Kolter, R., Genetic analysis of *Escherichia coli* biofilm formation: roles of flagelia, motility, chemotaxis and type I pili, Molecular Microbiology, Oct. 1998, 30(2): 285-293.

Hsu, Y. et al., Proliferative inhibition, cell-cycle dysregulation, and induction of apoptosis by ursolic acid in human non-small cell lung cancer A549 cells, Life Sci., Sep. 24, 2004, 75: 2303-2316.

Both, D. et al., Liposome-encapsulated ursolic acid increases ceramides and collagen in human skin cells, Arch Dermatol. Res., 2002, 293: 569-575.

Cardenas, C. et al., Effects of ursolic acid on different steps of the angiogenic process, Biochem. Biophys. Res. Commun., Jul. 23, 2004, 320: 402-408.

Hesse, H. et al., Molecular analysis and control of cysteine biosynthesis: integration of nitrogen and sulphur metabolism, J. Exp. Bot., Jun. 2004, 55(401): 1283-1292.

Murakami, S. et al., Ursolic acid, an antagonist for transforming growth factor (TGF) beta 1, FEBS Lett., May 21, 2004, 566: 55-59.

Abe, F., et al., Ursolic acid as a trypanocidal constituent in rosemary, Biol. Pharm. Bull., Nov. 2002, 25(11): 1485-1487.

Stanley, N. et al., Identification of Catabolite Repression as a Physiological Regulator of Biofilm Formation by *Bacillus subtilis* by Use of DNA Microarrays, Journal of Bacteriology, Mar. 2003, 185(6): 1951-1957.

Xavier, K. And Bassler, B., LuxS quorum sensing: more than just a numbers game, Current Opinion in Microbiology, 2003, 6: 191-197.

Jackson, D. et al., Catabolite Repression of *Escherichia coli* Biofilm Formation, Journal of Bacteriology, Jun. 2002, 184(12): 3406-3410.

Auger, S. et al., Global Expression Profile of *Bacillus subtilis* Grown in the Presence of Sulfate or Methionine, Journal of Bacteriology, Sep. 2002, 184(18): 5179-5186.

Lilic, M. et al., Identification of the CysB-regulated gene, *hslJ*, related to the *Escherichia coli* novobiocin resistance phenotype, FEMS Microbiology Letters, 2003, 224: 239-246.

Leyh, T. et al., The DNA Sequence of the Sulfate Activation Locus from *Escherichia coli* K-12, The Journal of Biological Chemistry, May 25, 1992, 267(15): 10405-10410.

Sauer, K. et al., *Pseudomonas aeruginosa* Displays Multiple Phenotypes during Development as a Biofilm, Journal of Bacteriology, Feb. 2002, 184(4): 1140-1154.

Lockowska, A. et al., Identification of activating region (AR) of *Escherichia coli* LysR-type transcription factor CysB and CysB contact site on RNA polymerase alpha subunit at the *cysP* promoter, Molecular Microbioloy, 2004, 53(3): 791-806.

Lochowska, A. et al., Functional Dissection of the LysR-type CysB Transcriptional Regulator, The Journal of Biological Chemistry, Jan. 19, 2001, 276(3): 2098-2107.

Quan, J. et al., Regulation of carbon utilization by sulfur availability in *Escherichia coli* and *Salmonella typhimurium*, Microbiology, 2002, 148: 123-131.

Van Der Ploeg, J. et al., Functional analysis of the *Bacillus subtilis cysK* and *cysJI* genes, FEMS Microbiology Letters, 2001, 201: 29-35.

Parry, J. and Clark, D., Identification of a CysB-regulated gene involved in glutathione transport in *Escherichia coli*, FEMS Microbiology Letters, 2002, 209: 81-85.

"Antibacterial Program" from Sequoia Sciences' website located at www.sequoiasciences.com/Antibacterials.htm, Oct. 26, 2004, pp. 1-2.

Elvers et al., Biofilms and Biofouling, 2nd ed., vol. 1, Academic Press, San Diego, CA.

Beloin, C., et al., Finding gene-expression patterns in bacterial biofilms, Trends in Microbiology, Jul. 2005, pp. 4022-4034, vol. 13 No. 1, Elsevier Science Ltd.

Mah Thien-Fah, C. et al., Mechanism of biofilm resistance to antimicrobial agents, Trends in Microbiology, Jan. 2001, pp. 34-39, vol. 9 No. 1, Elsevier Science Ltd.

Schembri, M., et al., An attractive surface: gram-negative bacterial biofilms, Science's Stke, May 2002, pp. 1-8, vol. 2002 No. 132.

U.S. Appl. No. 11/479,095, filed Jun. 30, 2006 Eldridge, Gary R.

U.S. Appl. No. 12/327,349, filed Dec. 3, 2008, Eldridge et al.

Adnyana et al., J. Nat. Prod., 2001, vol. 64, pp. 360-363 (Abstract).

Arevalo-Ferro, C. et al., Biofilm formation of *Pseudomonas putida* IsoF: the role of quorum sensing as assessed by proteomics, Systematic and Applied Microbiology, 2005, vol. 28, 87-114.

Begum et al., Triterpenoids from the Leaves of *Eucalyptus camaldulensis* var. *obtusa*, J. Nat. Prod. 1997, 60, pp. 20-23 (Abstract).

Chambers 21st Century Dictionary, Chambers Harrap Publishers Limited 2001, Retrieved Jul. 7, 2008, from http://www.credoreference.com/entry/1215201.

Chaturvedula et al., A New Ursane Triterpene from *Monochaetum vulcenicum* that Inhibits DNA Polymerase β Lyase, J. Nat. Prod. 2004, 67, pp. 889-901 (Abstract).

Cywes, C. et al., Group A *Streptococcus* tissue invasion by CD44-mediated cell signaling, Nature, 2001, 414, pp. 648-652.

Darouiche, R. et al., A Comparison of Two Antimicrobial-impregnated Central Venous Catheters, New Engl. Jour. Med., 1999, 340(1), pp. 1-8.

Datsenko and Wanner, One-step inactivation of chromosomal genes in *Escherichia coli* K-12 using PCR products, PNAS, Jun. 6, 2000, 97(12), pp. 6640-6645.

Demuth, D. et al., Discrete Protein Determinant Directs the Species-Species Adherence of *Porphyromonas gingivalis* to Oral *Streptococci*, Infection and Immunity, 2001, 69(9), pp. 5736-5741.

Edwards, J. et al., The role of lipooligosaccharide in *Neisseria gonorrhoeae* pathogenesis of cervical epithelia: lipid A serves as a C3 acceptor molecule, Cellular Micro., 2002, 4(9), pp. 585-598.

Hardy, G. et al., The Pathogenesis of Disease Due to Nontypeable *Haemophilus influenzae*, Methods Mol. Med., 2007, 71, M. Herbort © Humana Press Inc., Totawa, NJ, USA, pp. 1-28.

Honda, T. et al., Novel Synthetic Oleanane Triterpenoids: A Series of Highly Active Inhibitors of Nitric Oxide Production in Mouse Macrophages; Bioorganic & Medicinal Chemistry Letters, Elsevier Science Ltd., 1999, 9, pp. 3429-3434.

Hu, J. F. et al., Antibacterial, Partially Acetylated Obigorhamnosides from *Cleistopholis patens*, J. Nat. Prod., American Chemical Society and American Society of Pharmacognosy, 2006, 69, pp. 585-590.

Hu, J. F. et al., Cyclolignans from *Scyphocephalium ochocoa* via high-throughput natural product chemistry methods; Phytochemistry, Elsevier Ltd., 2005, 66, pp. 1077-1082.

Hu, J. F. et al., Application of Capillary-scale NMR for the Structure Determination of Phytochemicals, Phytochem. Anal., John Wiley & Sons, Ltd., 2005, 16, pp. 127-133.

Hu, J. F. et al., Miniaturization of the Structure Elucidation of Novel Natural Products—Two Trace Antibacterial Acylated Caprylic Alcohol Gylcosides from *Arctostaphylosis pumila*, Planta Med., 2005, 71, pp. 176-180.

Silverman, R. B., The Organic Chemistry of Drug Design and Drug Action, 2nd Ed., Elsevier Academy Press, 2004.

Wei, Y. et al., Journal of Bacteriology, 2001, vol. 183, No. 2, pp. 545-556.

Yoo, H-D. et al., Suaveolindole, a New Mass-Limited Antibacterial Indolosesquiterpene from Greenwayodendron suaveolens Obtained via High-Throughput Natural Products Chemistry Methods, American Chemical Society and American Society of Pharmacognosy, J. Nat. Prod., published on web Jan. 8, 2005, vol. 68, No. 1, pp. 122-124.

Blast search of the cysB gene at the Microbial Genomics database at the National Center for Biotechnology Information (NCBI) of the National Institutes of Health (NIH), http://www.ncbi.nim.nih.gov/sutils/genom_table.cgi.

Results of search performed by NERAC for scientific articles regarding Biofilm, Jan. 28, 2005, pp. 1-40.

European Search Report for Application No. 0579135 dated Jun. 29, 2007, Publication No. EP1771558A2.

International Preliminary Report on Patentability completed on Jun. 5, 2007 for PCT/US05/32874 (WO06/031943).

International Preliminary Report on Patentability completed on Oct. 1, 2006 for PCT/US05/25016 (WO06/019926).

International Preliminary Report on Patentability completed on Oct. 18, 2006 for PCT/US05/24945 (WO06/019881).

International Preliminary Report on Patentability completed on Feb. 21, 2006 for PCT/US05/24946 (WO06/010147).

International Preliminary Report on Patentability completed on Aug. 7, 2006 for PCT/US06/10088 (WO06/102255).

Written Opinion of the International Searching Authority completed on Feb. 16, 2006 for PCT/US05/32874 (WO06/031943).

Written Opinion of the International Search Authority completed on Feb. 6, 2006 for PCT/US05/25016 (WO06/019926).

Written Opinion of the International Search Authority completed on Jan. 23, 2006 for PCT/US05/24945 (WO06/019881).

Written Opinion of the International Search Authority completed on Feb. 21, 2006 for PCT/US05/24946 (WO06/010147).

Written Opinion of the International Search Authority completed on Sep. 25, 2007 for PCT/US06/10088 (WO06/102255).

Office Action issued by the United States Patent and Trademark Office for U.S. Appl. No. 11/181,556 dated Oct. 6, 2008.

Peter Ettmayer, Medicinal Chemistry, Lessons Learned from Marketed and Investigational Prodrugs, 2004, 47(10): 2394-2404.

Sherry L. Morisette, "High-throughput crystallization: polymorphs, salts, co-crystals and solvates of pharmaceutical solids," Advanced Drug Delivery Reviews, 2004, vol. 56: 275-300.

J. Valentino Stella, Expert Opinion of Therapeutic Patents, Prodrugs as therapeutics, 2004, 14(3): 277-280.

Bernard Testa, Biochemical Pharmacology, Prodrug Research: futile or fertile?, 2004, vol. 68: 2097-2106.

Sudha R. Vippagunta, "Crystalline Solids," Advanced Drug Delivery Reviews, 2001, vol. 48: 3-26.

Wolff et al., Burger's Medicinal Chemistry, 5th Ed., 1994, vol. 1: 975-977.

European Search Report for Application No. 05791709.8 dated Oct. 10, 2007.

Ren, D. et al., Differential gene expression for investigation of *Escherichia coli* biofilm inhibition by plant extract ursolic acid, Applied and Environmental Microbiology, Washington, DC, US, Jul. 2005, vol. 71, No. 7: 4022-4034.

Kaplan, J. B., Methods for the treatment and prevention of bacterial biofilms, Expert Opinion on Therapeutic Patents, Ashley Publications, GB, 2005, vol. 15, No. 8: 955-965.

Donlan, Rodney M. et al., Biofilms: Survival mechanisms of clinically relevant microorganisms, Clinical Microbiology Reviews, Apr. 2002, vol. 15, No. 2:167-193.

Hall-Stoodley, Luanne et al., Bacterial biofilms: From the natural environment to infectious diseases, Nature Reviews Microbiology, Feb. 2004, vol. 2, No. 2: 95-108.

Byrn, et al., Solid State Chemistry of Drugs, Chapter 10; 2nd ed., 1999, pp. 232-247.

Ito, H., et al., Megastigmane glycosides and an acylated triterpenoid from *Eriobotrya japonica*, Jun. 2001, vol. 64, No. 6, pp. 737-740.

Office Action dated Apr. 9, 2009, for U.S. Appl. No. 11/081,240, pp. 1-12.

* cited by examiner

Ursolic acid

Asiatic acid

INHIBITION OF BIOFILM FORMATION

CROSS REFERENCE TO RELATED APPLICATIONS

This application claims priority from U.S. provisional patent application Ser. No. 60/587,680, filed on Jul. 14, 2004, and U.S. provisional patent application Ser. No. 60/609,763, filed on Sep. 14, 2004.

FIELD OF THE INVENTION

The invention relates to methods for reducing or inhibiting biofilm formation. The invention also relates to methods for modulating the expression of a cysB gene. Further, the present invention relates to methods for identifying genes involved in biofilm formation and for identifying biofilm inhibitors.

BACKGROUND OF THE INVENTION

Bacterial biofilms exist in natural, medical, and engineering environments. The biofilm may offer a selective advantage to a microorganism to ensure its survival, or allow it a certain amount of time to exist in a dormant state until suitable growth conditions arise. This selective advantage could pose serious threats to human health. For example, biofilms are involved in 65% of human bacterial infections. Biofilms are also involved in prostatitis, biliary tract infections, urinary tract infections, cystitis, pyelonephritis, lung infections, sinus infections, ear infections, acne, and chronic wounds.

Biofilms contribute to a variety of medical conditions. Each year in the United States alone, over 7 million patients receive medical device implants, including central venous catheters, endotracheal tubes, mechanical heart valves, pacemakers, and prosthetic joints. Approximately one-half of these patients develop nosocomial infections, and approximately 80,000 deaths per year are attributed to nosocomial infections. Biofilms provide a structural matrix that facilitates bacterial adhesion to the inert surfaces of medical device implants and venous catheters. Microscopic studies confirm that central venous catheters are coated by bacteria embedded in biofilms. Unfortunately, more than 1 million patients develop urinary tract infections from such catheters.

Some diseased tissues, such as tumors, are susceptible to bacterial colonization. Bacterial colonization has been identified in calcified human aneurysms, carotid plaques, femoral arterial plaques, and cardiac valves. Arterial calcification resembles infectious lesion formation in animal models of atherosclerosis. A toxin produced by Cag-A positive *Helicobacter pylori* colonization of the stomach could lead to tissue inflammation and lesions in the arterial walls resulting in atherosclerosis. Bacterial colonization could also lead to the formation of kidney stones. Eradication of bacteria, and the biofilms that protect them, from the diseased tissue enables the host's immune system and/or a pharmaceutical agent to reach the diseased tissue. For example, *clostridia* spores and attenuated *Salmonella typhimurium*, used to deliver therapeutic proteins to tumors, may be more effective if the biofilm did not exist or is removed.

Biofilms may also cause diseases, such as cystic fibrosis, or contribute to chronic symptoms. Chronic bacterial infections represent a serious medical problem in the United States. Antibiotics are typically used to treat both acute and chronic infections. In chronic bacterial infections, biofilms protect the bacteria from the antibiotics and the host's immune system, thus increasing the rates of recurring symptoms and resistance to the antibiotics. Researchers theorized that a biofilm gives bacteria a selective advantage by reducing the penetration of an antibiotic to the extent necessary to eradicate the bacteria. Through biofilms, the microbes can resist antibiotics at high concentrations, about 1 to 1.5 thousand times higher than necessary in the absence of biofilms. Not surprisingly, during an infection, bacteria surrounded by biofilms are rarely resolved by the host's immune defense mechanisms.

As discussed above, biofilms provide a protective barrier for bacteria, thus, allowing the bacteria to resist antibiotic treatments. Developers of antibiotics must face the continuous challenge of antibiotic resistance. Antibiotic resistance significantly hinders treatment of the medical condition. For example, microbial resistance to minocycline and rifampin, which are widely used to treat infections, is emerging. A 1998 study of an intensive care unit revealed that 6 out of 7 vancomycin-resistant enterococci were resistant to rifampin.

Biofilm inhibition offers numerous advantages. Bacteria have no known resistance to biofilm inhibitors. Thus, unlike antibiotics, biofilm inhibitors can be used repeatedly and effectively in the same patient and for the same medical condition. For example, biofilm inhibitors may be employed to treat, cure, or prevent acute or chronic infections. They may be used to control microorganisms residing on living tissues. They may also be used to cure, treat, or prevent arterial damage, gastritis, urinary tract infections, cystitis, otitis media, leprosy, tuberculosis, benign prostatic hyperplasia, chronic prostatitis, chronic infections of humans with cystic fibrosis, osteomyelitis, bloodstream infections, skin infections, open wound infections, and any acute or chronic infection that involves or possesses a biofilm.

Biofilm inhibitors can act specifically on the biological mechanisms that provide bacteria protection from antibiotics and from a host's immune system. In one study of urinary catheters, rifampin was able to clear planktonic or suspended methicillin-resistant *Staphylococcus aureus*, but was unable to eradicate the bacteria in a biofilm. Current treatment of infections, e.g. nosocomial infections, often requires sequential or simultaneous administration of a combination of products, such as amoxicillin/clavulanate and quinupristin/dalfopristin. A direct inhibition of the bacterial mechanisms used to form biofilms may help reduce blood stream infections (BSI).

In addition, a direct inhibition of the bacterial mechanisms used to form biofilms delays the onset of microbial resistance to antibiotics, and possibly, reduces the emergence of multi-resistant bacteria. Another approach to reducing or inhibiting biofilm formation is to apply evolutionary pressure to the bacterial growth mechanisms. Accordingly, extensive research are devoted to elucidating the genes, especially the critical players, that are involved in controlling biofilm formation.

Accordingly, for the reasons discussed above and others, there continues to be a need for a means to control biofilm and its formation.

SUMMARY OF INVENTION

The present invention provides a method for reducing or inhibiting a biofilm comprising modulating expression of a cysB gene in a cell capable of biofilm formation.

Further, the present invention provides a method for modulating the expression of a cysB gene comprises contacting a cell capable of biofilm formation with a composition comprising a compound selected from the group consisting of ursolic acid or asiatic acid, or a pharmaceutically acceptable salt of such compound, a hydrate of such compound, a solvate of such compound, an N-oxide of such compound, or a combination thereof.

The present invention further provides a method for identifying a gene or genes involved in biofilm formation comprising a) mutating a gene, wherein the gene is a cysB gene or a gene related to cysB in at least one cell capable of biofilm formation; b) contacting the cell with a compound selected from the group consisting of ursolic acid or asiatic acid or an analog of such compound; c) contacting at least one wild-type cell with the compound chosen in step b); and d) measuring the biofilm formation by the cell and the biofilm formation by the wild-type cell, wherein a modulation of the biofilm formation by the cell compared to the biofilm formation by the wild-type cell indicates the involvement of the gene in biofilm formation.

The present invention provides a method for identifying an agent that reduces or inhibits biofilm formation comprising contacting a cell capable of biofilm formation with the agent; providing a reporter marker linked to a gene, wherein the gene is a cysB gene or a gene related to cysB, wherein the reporter marker allows detection of the expression of the gene; and detecting modulation of the expression of the gene or of its gene product.

DESCRIPTION OF THE INVENTION

Figure 1:
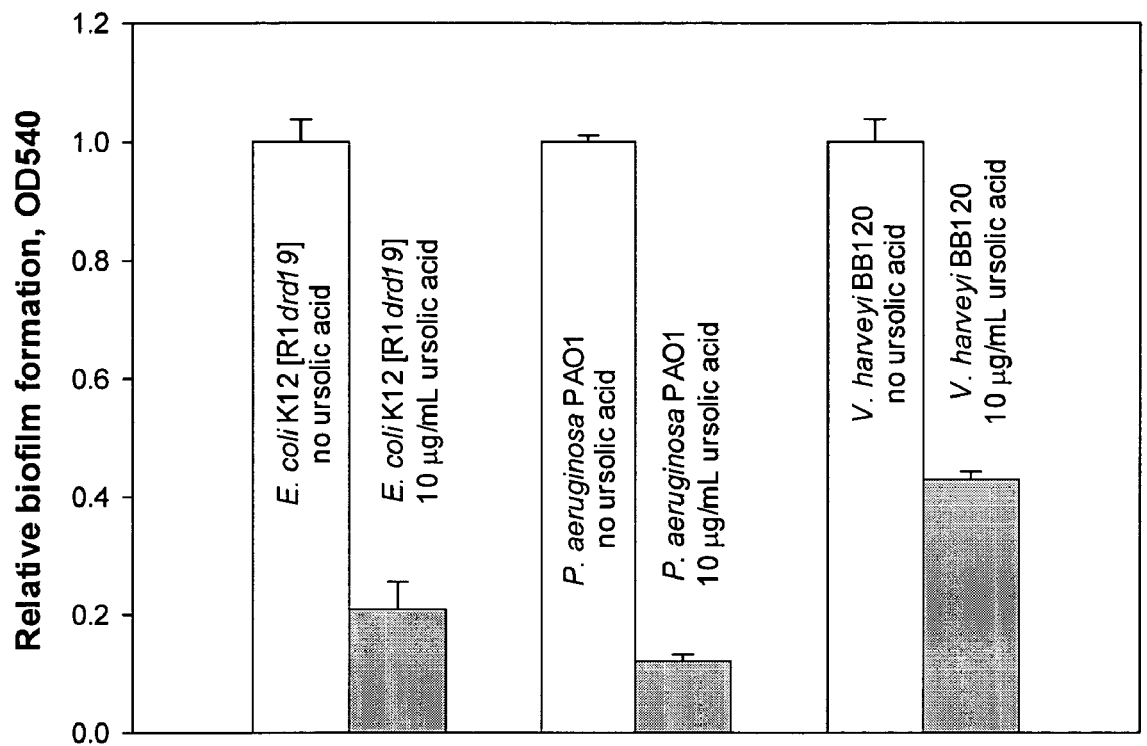
FIG. 1 shows the inhibition of biofilm formation in *E. coli* K12, *P. aeruginosa* PAO1, and *V. harveyi* BB120 with ursolic acid.

Definitions:

"Acceptable carrier" refers to a carrier that is compatible with the other ingredients of the formulation and is not deleterious to the recipient thereof.

"Reducing or inhibiting" in reference to a biofilm refers to the prevention of biofilm formation or growth, reduction in the rate of biofilm formation or growth, partial or complete inhibition of biofilm formation or growth.

"Modulates" or "modulating" refers to up-regulation or down-regulation of a gene's replication or expression.

Description:

The present invention provides a method for reducing or inhibiting a biofilm comprising modulating the expression of a cysB gene in a cell capable of biofilm formation.

Biofilm inhibitors can be used to treat diseases caused by bacteria existing in biofilms. For example, the inhibitors can contribute to the treatment of cystic fibrosis. In cystic fibrosis, *Pseudomonas aeroginosa* reside on the lungs of cystic fibrosis patients. The inhibitors can prevent, reduce, or eradicate the biofilm of *Pseudomonas aeroginosa*. In addition, biofilm inhibitors can prevent the attachment of *Helicobactor pylori* to gastric epithelial cells in patients with gastritis. This prevents the bacteria's invasion into these epithelial cells. By preventing *H. pylori* attachment to gastric epithelial cells, biofilm inhibitors also prevent or reduce the risks associated with subsequent virulence factors, such as arterial damage which may lead to a stroke. Moreover, biofilm inhibitors can also be used to treat urinary tract infections. *E. coli* reside intracellularly in bladder cells. The *E. coli* resist conventional antibiotics and evade the host's immune systems. The biofilm inhibitors can prevent, control, reduce, or eradicate the *E. coli*. The biofilm inhibitors prevent or disrupt the attachment of *E. coli* to uroplakin or the proteins of the tight junctions of umbrella cells of the bladder, thereby potentially controlling the re-occurrence of urinary tract infections.

Biofilm formation involves biological pathways conserved among different species of bacteria. For example, different species of bacteria share a common global regulator in the formation and maintenance of biofilms. Jackson et. al. showed catabolite repression induced by glucose caused 30% to 95% reduction in biofilms among *E. coli*, *Citrobacter freundii*, *Klebsiella pneumoniae*, and *Salmonella enterica Typhimurium*. (Jackson, et al. *J. Bacteriol.* 2002, 184, 3406-3410). A bacterial autoinducer signal, AI-2, has been shown to be involved in the formation of biofilms. AI-2 and genes responsive to this signal have been identified in a variety of bacteria. Preferably, in an embodiment of the present invention, the biofilm is reduced or inhibited by modulating expression of cysB in *Escherichia coli*, *Proteus mirablis*, *Francisella tularensis*, *Vibrio* sp., *Pseudomonas aeruginosa*, *V. harveyi*, *Pseudomonas* sp., *Salmonella* sp., *Haemophilus influenzae*, *Borrelia* sp., *Neisseria* sp., *Bacillus* sp., *Burkholderia* sp., *Klebsiella* sp., or *Yersinia pestis*. Still, preferably, the biofilm is reduced or inhibited by modulating expression of cysB in a Gram-negative bacteria.

CysB may be modulated in a number of ways. For example, N-acetyl-serine and sulfur limitation up-regulate cysB. Lochowska, A. et al., Functional Dissection of the LysR-type CysB Transcriptional Regulator. *J. Biol. Chem.* 2001, 276, 2098-2107. In addition, like other LysR type regulators, cysB can repress itself. Lilic, M. et al., Identification of the CysB-regulated gene, hslj, related to the *Escherichia coli* novobiocin resistance phenotype. *FEMS Micro. Letters.* 2003, 224, 239-246.

The disclosure herein describes another means to modulate cysB. The present invention, therefore, also provides a method for modulating the expression of a cysB gene comprising contacting the cell with a composition comprising a compound selected from the group consisting of ursolic acid or asiatic acid, or a pharmaceutically acceptable salt of such compound, a hydrate of such compound, a solvate of such compound, an N-oxide of such compound, or a combination thereof.

The disclosure herein describes the discovery that the cysB gene, a transcriptional regulator of the biosynthesis of cysteine, is involved in biofilm formation. (Verschueren, K. H. G., *Crystallization of full-length CysB of Klebsiella aerogenes, a LysR-type transcriptional* regulator, BIOLOGICAL CRYSTALLOGRAPHY D57:260-262, 2001). As demonstrated in the examples herein, the removal of cysB from *E. coli* results in a significant reduction of biofilm formation in *E. coli* as compared to wild-type *E. coli*. The cysB protein is a transcriptional regulator of the LysR family of genes. The transcriptional regulators of this family have helix-turn-helix DNA binding motifs at their amino-terminus. The cysB protein is required for the full expression of the cys genes, which is involved in the biosynthesis of cysteine.

The cysB gene is genetically conserved among different species of bacteria, and more specifically Gram-negative bacteria. Verschueren, et al., *Acta Cryst.* (2001) D57, 260-262; Byrne et al., J. Bacteriol. 1988 170 (7), p. 3150-3157. In fact, cysB is conserved among *Pseudomonas* sp. including, but not limited to, *P. aeruginosa*, *P. putida*, and *P. syringae*. (http:// www.ncbi.nlm.nih.gov/sutils/genom_table.cgi. Blast search of the cysB gene at the Microbial Genomics database at the National Center for Biotechnology Information (NCBI) of the National Institutes of Health (NIH)). The cysB gene is also genetically conserved among the following species of bacteria: *Vibrio* sp. (e.g. *V. harveyi* and *V. cholera*), *Proteus mirablis*, *Burkholderia* sp. (e.g. *B. fongorum*, *B. mallei*, and *B. cepacia*), *Klebsiella* sp., *Haemophilus influenza*, *Neisseria meningitides*, *Bordetella pertussis*, *Yersinia pestis*, *Salmonella typhimurium*, and *Acinetobacter* sp. (http://www.ncbi.nlm.nih.gov/sutils/genom_table.cgi. Blast search of the cysB gene at the Microbial Genomics database at NCBI of NIH). The cysB gene is also genetically conserved among the Gram-positive bacteria of *Bacillus* sp. including, but not limited to, *B. subtilis*, *B. cereus*, and *B. anthracis*. (http://www.ncbi.nlm.nih.gov/sutils/genom_table.cgi. Blast search of the cysB gene at the Microbial Genomics database at NCBI of NIH; van der Ploeg, J. R.; FEMS Microbiol. Lett. 2001, 201, p. 29-35).

In one embodiment of the present invention, the cell is selected from a group consisting of Gram-negative bacteria. In another embodiment of the invention, the cell is selected from a group consisting of *Escherichia coli*, *Proteus mirablis*, *Francisella tularensis*, *Vibrio* sp., *Pseudomonas aeruginosa*, *V harveyi*, *Pseudomonas* sp., *Salmonella* sp., *Haemophilus influenzae*, *Borrelia* sp., *Neisseria* sp., *Bacillus* sp., *Burkholderia* sp., *Klebsiella* sp., and *Yersinia pestis*. Preferably, the cell is *E. coli*, *Pseudomonas aeruginosa*, or *V. harveyi*. As demonstrated in Example 2, ursolic acid reduces or inhibits the formation of biofilms in *E. coli*, *P. aeruginosa*, and *V. harveyi*. Using a similar method described in Example 2, asiatic acid was shown in Example 6 to reduce or inhibit biofilm formation in *E. coli*.

Another embodiment of the present invention is a method for modulating the expression of cysD, cysI, cysJ, and/or cysK. Cys B controls the cysDIJK family of genes at the transcriptional level. Leyh, T., et al. *J. Biol. Chem.* 1992, 267(15), p. 10405-10410. Administration of ursolic acid down-regulates the expression of cysB and certain genes under its transcriptional control, such as cysDIJK, while administration of asiatic acid up-regulates the expression of cysB and certain genes under its transcriptional control. By modulating the expression of cysB, ursolic acid and asiatic acid reduce or inhibit biofilm formation.

Members of the family of LysR transcriptional regulators have been demonstrated to regulate diverse metabolic processes. cysB exhibits direct control of the biosynthesis of cysteine. Verschueren et al., at p. 260. The cysB gene is involved, directly or indirectly, in glutathione intracellular transport, carbon source utilization, alanine dehydrogenases, and the arginine dependent system. YbiK is under the direct control of cysB and participates in glutathione intracellular transport. The data in example 1 demonstrates the down-regulation of ybiK by contacting a bacterial cell with ursolic acid. The down-regulation of ybiK in Example 1 of the specification further supports that ursolic acid down-regulates cysB. In an embodiment of the invention, ursolic acid or asiatic acid modulates the expression of ybiK.

Figure 9:
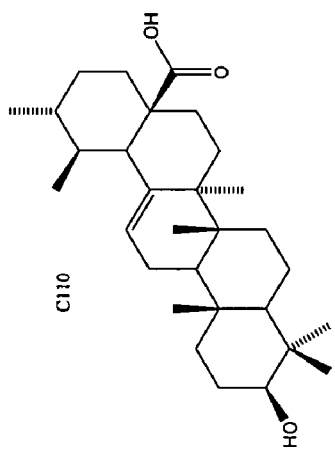
FIG. 9 shows the chemical structures of ursolic acid and asiatic acid.
Figure 9:
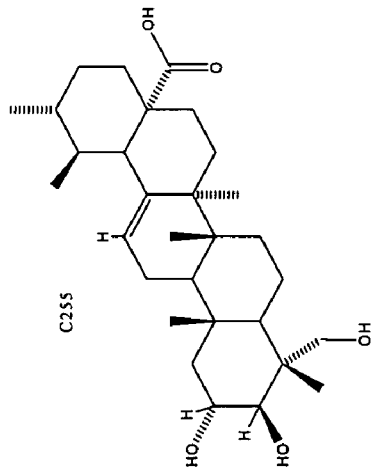

FIG. 9 shows the chemical structures of ursolic acid (C110) and asiatic acid (C255). Ursolic acid (UA) is a pentacyclic triterpene compound isolated from many type of medicinal plants and is present in the human diet. It has been reported to possess a wide range of pharmacological benefits, including anti-cancer and anti-aging therapies. See e.g. Hsu et al., Life Sci. 75(19):2303-2316, Sep. 24, 2004 and Both et al., Arch Dermatol. Res. 293(11):569-575, January 2002. Ursolic acid has also been identified as an antagonist for transforming growth factor (TGFβ1). Murakami et al., FEBS Lett. 566(1-3):55-59, May 21, 2004. However, before the disclosure herein, neither ursolic acid nor asiatic acid has been reported to modulate the expression of the cysB gene. Neither have ursolic acid nor asiatic acid been reported to reduce or inhibt biofilm formations. Analogs of ursolic acid (C110) and asiatic acid (C255) are expected to also modulate the expression of the cysB gene. FIGS. 4-8 show examples of analogs of ursolic acid and asiatic acid.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

Another means to control biofilm formation is to understand the underlying genetics involved. As it turns out, a complex web of genes regulates the formation and maintenance of biofilms by bacteria. For instance, Sauer et al. demonstrated that approximately 525 proteins are differentially regulated during the different stages of biofilm development in *Pseudomonas aeruginosa*. Sauer et al., J. Bacteriol. November 2004; 186(21):7312-26. Stanley et al. demonstrated that approximately 519 proteins are differentially regulated during the first 24 hours of biofilm formation in *Bacillus subtilis*. Stanley, N. R. et al. *J. Bacteriol.* 2003, 185, 1951-1957. While numerous genes may be involved in a variety of biological pathways, only a few genes play critical roles. Researchers spend considerable amount of effort determining which gene(s) are critical or essential in the biological pathways involved in various stages of biofilm formation and maintenance. The disclosure herein describes the discovery of the genes involved in biofilm formation, such as cysB, cysD, cysI, cysJ, cysK gene(s), and ybiK and the compounds that modulate these genes and reduce or inhibit biofilm formation.

Prior to the present invention, researchers look for genes involved in biofilm formation by manipulating various factors, such as media condition, experimental temperature, random gene knock-out, and glucose level. These processes can be tedious, time-consuming, and costly. See e.g. Sauer et al., J. Bacteriol. November 2004; 186(21):7312-26; Ren et al., Applied and Environmental Microbiology, April 2004, 70(4): 2038-2043; Verschueren et al., Biological Crystallography, 2001, D57:260-262; Pratt, L. A. and Roberto Kolter, Molecular Microbiology, October 1998, 30(2):285-293. The present invention provides a method for identifying a gene or genes involved in biofilm formation comprising a) mutating a gene, wherein the gene is a cysB gene or a gene related to cysB in at least one cell capable of biofilm formation; b) contacting the cell with a compound selected from the group consisting of ursolic acid or asiatic acid or an analog of such compound; c) contacting at least one wild-type cell with the compound chosen in step b); and d) measuring the biofilm formation by the cell and the biofilm formation by the wild-type cell, wherein a modulation of the biofilm formation by the cell compared to the biofilm formation by the wild-type cell indicates the involvement of the gene in biofilm formation.

As described herein, cysB is involved in biofilm formation. It controls the biosynthesis of cysteine. Verschureren et al., at p. 260. Using cysB, standard methods can be used to identify other genes or gene products under its control that are involved in biofilm formation. For example, expression of cysB may be modulated while either modulating or monitoring the expressions of the other genes suspected of being involved in biofilm formation. This method identifies a gene's (or its gene product) involvement in biofilm formation. A person of ordinary skill in the art may perform additional tests to confirm the gene's (or its gene product) involvement in biofilm formation. Expressions of either cysB or genes under its control, such as cysDIJK family of genes, can be modulated, and using DNA microarrays (as demonstrated in the examples) to determine direct or indirect effects as a result of the modulation. An inhibitor can also be used during these experiments to promote modulation of specific genes or gene products.

The present invention also provides a method for identifying novel agents that reduce or inhibit the formation of biofilms. As described in the specification, the modulation of the expression of cysB inhibits the formation of biofilms. cysB is the global regulator of the biosynthesis of cysteine which directly controls the expression of the genes involved in this process. The invention allows one skilled in the art of screening compounds in drug discovery to measure the modulation of a gene, wherein the gene is a cysB gene or a gene related to cysB, during the screening of compounds as a novel detection method for the reduction or inhibition of biofilms. This method provides various advantages over current screening strategies. Traditionally, the process of identifying biofilm inhibitors involves exposing at least one bacterial cell to a compound and then measuring the decrease in the formation of biofilms 24 to 72 hours after exposure. The reduction in biofilm formation is quantified using crystal violet stain, which can be problematic. As described in the literature, after the bacteria are exposed to the compounds, they are rinsed for a variable amount of time, stained for a certain amount of time with crystal violet stain, rinsed with solvents or combinations of solvents, and analyzed by determining optical densities of the crystal violet solutions compared to the controls. (Pratt, L. A. et al. Mol. Micro. 1998, 30(2), p. 285-298.). Therefore, measurement of the inhibition of biofilm formation can be laborious and can yield unreliable results. Taking advantage of the discovery described herein that modulation of a cysB gene is involved in biofilm formation, the present inventions provides a simple, fast, and inexpensive method of detecting the inhibition of biofilms. The method involves the detection of the modulation of a gene, wherein the gene is a cysB gene or a gene related to cysB involved in biofilm formation. A reporter system is linked to the gene or its gene product. Specifically, the modulation of the cysB gene, a gene related to a cysB gene or its gene product can be detected with a reporter, e.g., a green fluorescent protein, antibiotic, radioactive isotope, or fluorescent dye. Accordingly, the present invention provides a superior method to identify novel biofilm inhibitors than presently available in the art.

Biofilms may also adhere to surfaces, such as pipes and filters. Deleterious biofilms are problematic in industrial settings because they cause fouling and corrosion in systems such as heat exchangers, oil pipelines, and water systems. Elvers et al., Biofilms and Biofouling, 2$^{nd}$ ed., vol. 1, Academic Press, San Diego, Calif. Biofilm inhibitors can be employed to prevent microorganisms from adhering to surfaces which may be porous, soft, hard, semi-soft, semi-hard, regenerating, or non-regenerating. These surfaces include, but are not limited to, polyurethane, metal, alloy, or polymeric surfaces in medical devices, enamel of teeth, and cellular membranes in animals, preferably, mammals, more preferably, humans. The surfaces may be coated or impregnated with the biofilm inhibitors prior to use. Alternatively, the surfaces may be treated with biofilm inhibitors to control, reduce, or eradicate the microorganisms adhering to these surfaces.

The descriptions herein is not intended to limit the scope of the present invention, but only to demonstrate the far reaching utility of the invention to those skilled in the art. All references cited herein are hereby incorporated by reference in their entirety.

EXAMPLES

Example 1

Inhibition of biofilm formation by *E. coli* K12 [R1drd19], *P. aeruginosa* PAO1, and *V. harveyi* BB120 by the addition of 10 µg/mL ursolic acid. For *E. coli* K12 [R1drd19], data were collected 16 hours after addition of ursolic acid to a 24 hour biofilm in LB medium; for *P. aeruginosa* PAO1, data were collected 18 hours after addition of ursolic acid with inoculation in LB medium plus 1% sodium citrate; and for *V. harveyi* BB120, data were collected 18 hours after addition of ursolic acid with inoculation in M9 medium. All biofilm mass readings at OD540 were normalized based on the reading of wild type without ursolic acid which was normalized to 1. One standard deviation is shown. The results are shown in FIG. 1.

Example 2

Figure 2:
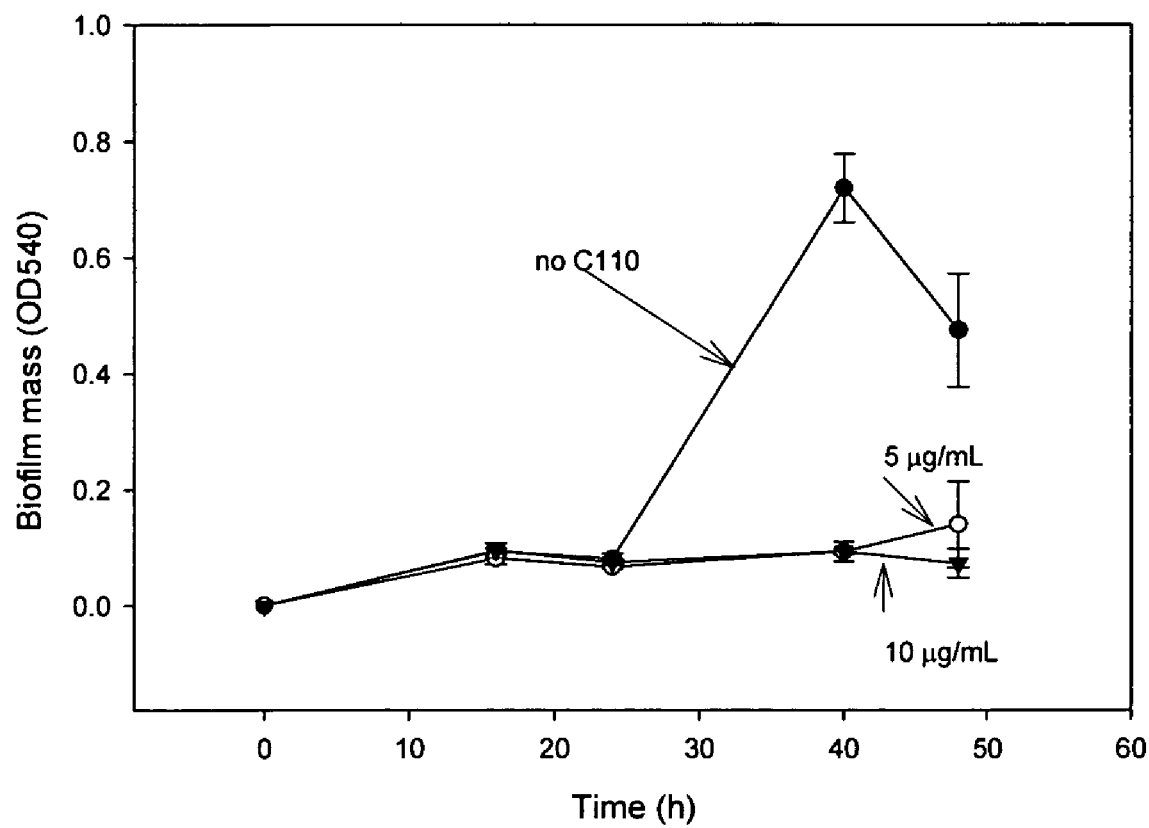
FIG. 2 shows the inhibition of air-liquid interface biofilm with ursolic acid.

Example 1 was repeated, except ursolic acid was added with inoculation in *E. coli* JM109 grown in LB 0.2% glucose. Ursolic acid inhibited air-liquid interface biofilm. The results are shown in FIG. 2.

Example 3

To identify the genes controlled by ursolic acid, *E. coli* K12 was grown in LB medium overnight, diluted 1:100 in fresh LB supplemented with 0, 10, or 30 µg/mL ursolic acid. The same amount of ethanol was supplemented to eliminate solvent effects. The cultures were grown to an $OD_{600}$ of 0.9. The cells were centrifuged in a microcentrifuge for 15 seconds at 20,000×g in mini bead beater tubes (Biospec, Bartlesville, Okla.) that were cooled to −80° C. before sampling. The cell pellets were flash frozen in a dry ice-ethanol bath and stored at −80° C. until RNA isolation.

To lyse the cells, 1.0 mL RLT buffer (Qiagen, Inc., Valencia, Calif.) and 0.2 mL 0.1 mm zirconia/silica beads (Biospec) were added to the frozen bead beater tubes containing the cell pellets. The tubes were closed tightly and beat for 30 seconds at the maximum speed in a mini bead beater (cat. no. 3110BX, Biospec). The total RNA was isolated by following the protocol of the RNeasy Mini Kit (Qiagen) including an on-column DNase digestion with RNase-free DNase I (Qiagen). $OD_{260}$ was used to quantify the RNA yield. $OD_{260}/OD_{280}$ and 23S/16S rRNA were measured using a 2100 Bioanalyzer (Agilent Technologies, Palo Alto, Calif.) to check the purity and integrity of RNA (RNeasy Mini handbook, Qiagen).

The *E. coli* DNA microarrays were prepared as described previously by Wei, Y. et al (Journal of Bacteriology, 2001, 183 (2) p. 545-556). Each gene probe was synthesized by PCR and has the size of the full open reading frame (200-2000 nt).

The double-strand PCR products were denatured in 50% dimethyl sulfoxide and spotted onto aminosilane slides (Full Moon Biosystems, Sunnyvale, Calif.) as probes to hybridize with the mRNA-derived cDNA samples. It has been shown that each array can detect 4228 of the 4290 *E. coli* ORFs. Each gene has two spots per slide.

Briefly, the total RNA from the *E. coli* K12 samples grown with and without ursolic acid was first converted into labeled cDNA. Then the cDNA samples (6 µg of each) were each labeled with both Cy3 and Cy5 dyes to remove artifacts related to different labeling efficiencies; hence, each experiment needed at least two slides. The Cy3-labeled sample without ursolic acid and the Cy5-labeled ursolic acid sample (with 10 or 30 µg/mL ursolic acid) were hybridized on the first slide. Similarly, the Cy5-labeled sample without ursolic acid and the Cy3-labeled ursolic acid sample were hybridized on the second slide. Since each gene has two spots on a slide, the two hybridizations generated eight data points for each gene (four points for the sample without ursolic acid and four points for the ursolic acid sample). The microarray experiments with dye-swapping were repeated for both concentrations of ursolic acid.

The cDNA samples of *E. coli* DH5α treated with FCM or 0.5×LB (6 µg of each) were each labeled with both Cy3 and Cy5 dyes to remove artifacts related to different labeling efficiencies; hence, each experiment required at least two slides. The Cy3-labeled FCM sample and Cy5-labeled 0.5× LB sample were hybridized on the first slide. Similarly, the Cy5-labeled FCM sample and Cy3-labeled 0.5×LB sample were hybridized on the second slide. Since each gene has two spots on a slide, the two hybridizations generated eight data points for each gene (four points for the FCM sample and four points for the 0.5×LB sample). DNA microarrays for the *E. coli* DH5α treated with ACM or 0.5×LB were performed in an analogous manner.

The DNA microarrays were incubated in prehybridization solution (3.5×SSC [1×SSC is 0.15 M NaCl plus 0.015 M sodium citrate] [Invitrogen], 0.1% sodium dodecyl sulfate [SDS] [Invitrogen], and 0.1% bovine serum albumin [Invitrogen]) at 45° C. for 20 min. The arrays were rinsed with double-distilled water and were spun dry by centrifugation. Labeled cDNA (6 µg) was concentrated to 10 µl of total volume and was mixed with 10 µl of 4×cDNA hybridization solution (Full Moon Biosystems) and 20 µl of formamide (EM Science, Gibbstown, N.J.). The hybridization mix was heated to 95° C. for 2 min and was added to the DNA microarrays; each array was covered with a coverslip (Corning, Big Flats, N.Y.) and was incubated overnight at 37° C. for hybridization. When the hybridization was finished, the coverslips were removed in 1×SSC-0.1% SDS at room temperature, and the arrays were washed once for 5 min in 1×SSC-0.1% SDS at 40° C., twice for 10 min in 0.1×SSC-0.1% SDS at 40° C., and twice for 1 min in 0.1×SSC at 40° C. The arrays were quickly rinsed by dipping in room-temperature double-distilled water and were then spun dry by centrifugation. The hybridized slides were scanned with the Generation III Array Scanner (Molecular Dynamics Corp.). Readings at 570 and 670 nm was used to quantify the probes labeled with Cy3 and Cy5 separately. The signal was quantified with Array Vision 4.0 or 6.0 software (Imaging Research, St. Catherines, Ontario, Canada). Genes were identified as differentially expressed if the expression ratio was greater than 1.4 and the p-value (t-test) is less than 0.05. P-values were calculated on log-transformed, normalized intensities. Including the p-value criterion ensures the reliability of the induced/repressed gene list. Normalization was relative to the median total fluorescent intensity per slide per channel.

TABLE 1

*E. coli* K12 genes repressed by 10 and 30 µg/mL ursolic acid. The underlined ratios indicate the corresponding genes were significantly repressed by ursolic acid. The highlighted genes were repressed both by 10 and 30 µg/mL ursolic acid. ER is expression ratio and Pv is p-value.

| Gene | b# | 10 µg/mL ursolic acid ER | Pv | 30 µg/mL ursolic acid ER | Pv | Description |
|---|---|---|---|---|---|---|
| arsC | b3503 | −1.5 | 0.045 | 1.4 | 0.014 | enzyme, drug/analog sensitivity |
| b2789 | b2789 | −1.9 | 0.056 | −2.5 | 0.038 | putative D-glucarate permease (MFS family) |
| cspF | b1558 | −1.6 | 0.003 | −1.1 | 0.357 | cold shock-like protein |
| cspG | b0990 | −2.5 | 0.009 | −1.7 | 0.017 | homolog of *Salmonella* cold shock protein |
| cysB | b1275 | −1.7 | 0.038 | −1.4 | 0.018 | positive transcriptional regulator for cysteine regulon |
| cysD | b2752 | −2.5 | 9E-04 | −2.5 | 0.024 | central intermediary metabolism: sulfur metabolism |
| cysI | b2763 | −1.5 | 0.069 | −1.7 | 2E-04 | central intermediary metabolism: sulfur metabolism |
| cysJ | b2764 | −3.6 | 0.015 | −3.3 | 0.009 | central intermediary metabolism: sulfur metabolism |
| cysK | b2414 | −3.6 | 0.003 | −3.3 | 0.008 | amino acid biosynthesis: cysteine |
| frvR | b3897 | −5.4 | 0.006 | −2 | 0.175 | putative frv operon regulatory protein |
| gntU_1 | b3436 | −1.5 | 0.026 | −1.4 | 0.043 | transport of small molecules: carbohydrates, organic acids, alcohols |
| narH | b1225 | −1.6 | 0.002 | −1.4 | 0.028 | energy metabolism, carbon: anaerobic respiration |
| pheM | b1715 | −1.6 | 0.011 | 1 | 0.762 | aminoacyl tRNA synthetases, tRNA modification |
| pheP | b0576 | −1.5 | 0.021 | −1.1 | 0.499 | transport of small molecules: amino acids, amines |
| rimL | b1427 | −1.5 | 0.022 | 1 | 0.719 | enzyme, ribosomes - maturation and modification |
| rmf | b0953 | −1.5 | 0.003 | 1 | 0.662 | factor; ribosomes - maturation and modification |
| rpmI | b1717 | −1.6 | 0.007 | 1 | 0.708 | structural component, ribosomal proteins - synthesis, modification |
| slp | b3506 | −1.5 | 0.006 | −1.6 | 0.002 | outer membrane constituents |
| ugpB | b3453 | −1.4 | 0.045 | −1.5 | 0.021 | transport of small molecules: carbohydrates, organic acids, alcohols |
| ybiK | b0828 | −2.4 | 7E-04 | −2.2 | 0.005 | putative asparaginase |
| yhaD | b3124 | −1.6 | 0.025 | −2.6 | 0.009 | glycerate kinase I |
| yhaF | b3126 | −1.5 | 0.009 | −2.4 | 0.002 | alpha-dehydro-beta-deoxy-D-glucarate aldolase |
| yhaG | b3128 | −2 | 0.004 | −2.2 | 0.008 | (D)-galactarate dehydrogenase |
| b0309 | b0309 | −1.7 | 0.042 | −1.3 | 0.155 | orf, hypothetical protein |

TABLE 1-continued

E. coli K12 genes repressed by 10 and 30 µg/mL ursolic acid. The underlined ratios indicate the corresponding genes were significantly repressed by ursolic acid. The highlighted genes were repressed both by 10 and 30 µg/mL ursolic acid. ER is expression ratio and Pv is p-value.

| Gene | b# | 10 µg/mL ursolic acid | | 30 µg/mL ursolic acid | | Description |
|---|---|---|---|---|---|---|
| | | ER | Pv | ER | Pv | |
| b0484 | b0484 | −1.5 | 0.044 | −1.1 | 0.425 | putative enzyme, not classified |
| b0485 | b0485 | −1.8 | 0.009 | −1.3 | 0.019 | putative enzyme, not classified |
| b0829 | b0829 | −1.5 | 0.032 | −1.5 | 0.09 | putative transport; not classified |
| b1729 | b1729 | −5.6 | 0.003 | −2 | 0.133 | putative enzyme, not classified |
| b2379 | b2379 | −1.5 | 0.011 | 1 | 0.325 | putative enzyme, not classified |
| hdeA | b3510 | −1.7 | 0.008 | −1.4 | 0.008 | orf, hypothetical protein |
| hdeB | b3509 | −1.8 | 6E-04 | −1.4 | 0.01 | orf, hypothetical protein |
| yeeD | b2012 | −2.3 | 0.025 | −1.4 | 0.228 | orf, hypothetical protein |
| yeeE | b2013 | −13 | 0.006 | −2 | 0.182 | putative transport, not classified |
| yjeB | b4178 | −1.4 | 0.005 | 1 | 0.833 | orf, hypothetical protein |
| ybhG | b0795 | −1.4 | 0.013 | −1.4 | 0.002 | putative membrane, not classified |
| yhaU | b3127 | −1.9 | 0.074 | −4.2 | 0.003 | putative transport protein |

Example 4

Figure 3:
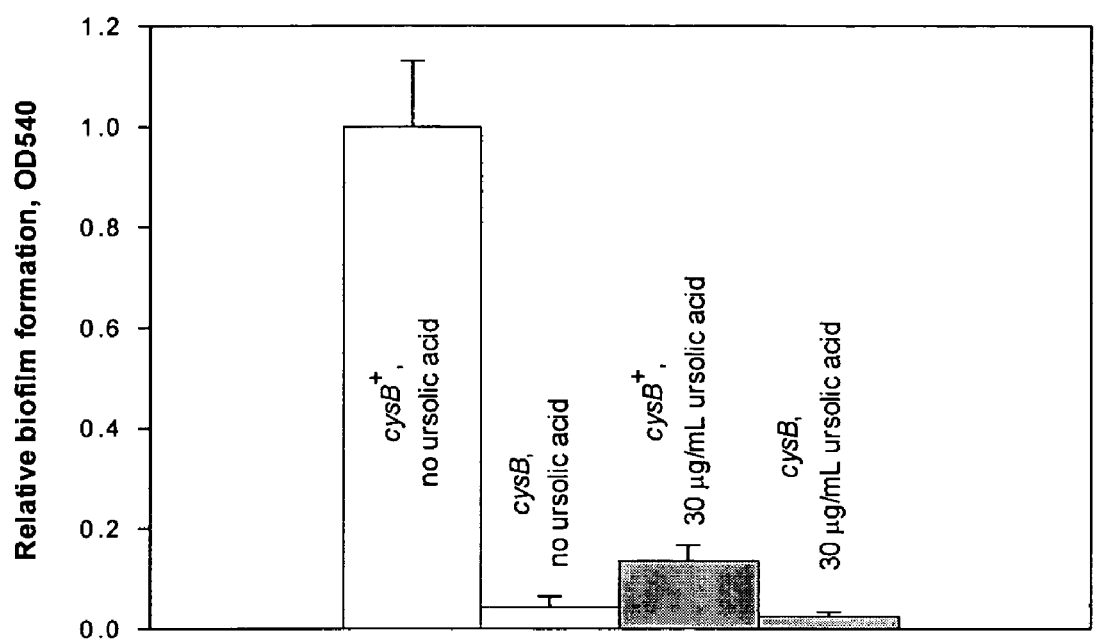
FIG. 3 shows a comparison of the inhibition of biofilm formation by wild-type *E. coli* and mutant *E. coli* (cys B mutation) with ursolic acid.
Figure 4:
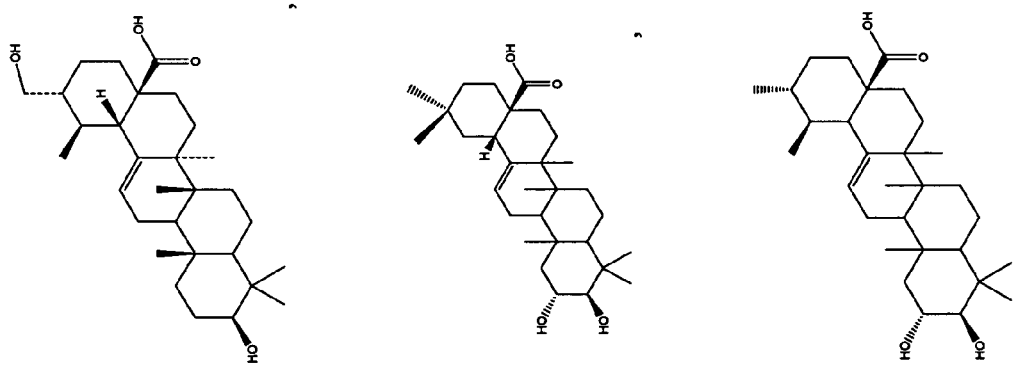
FIGS. 4-8 show analogs of ursolic acid and asiatic acid.
Figure 5:
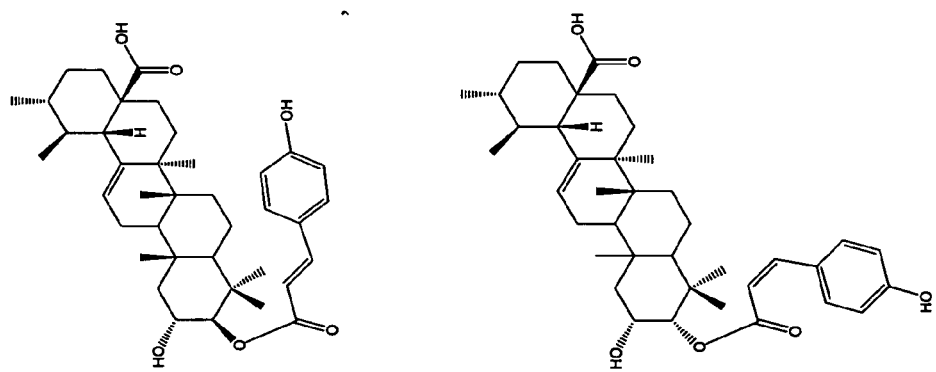
Figure 6:
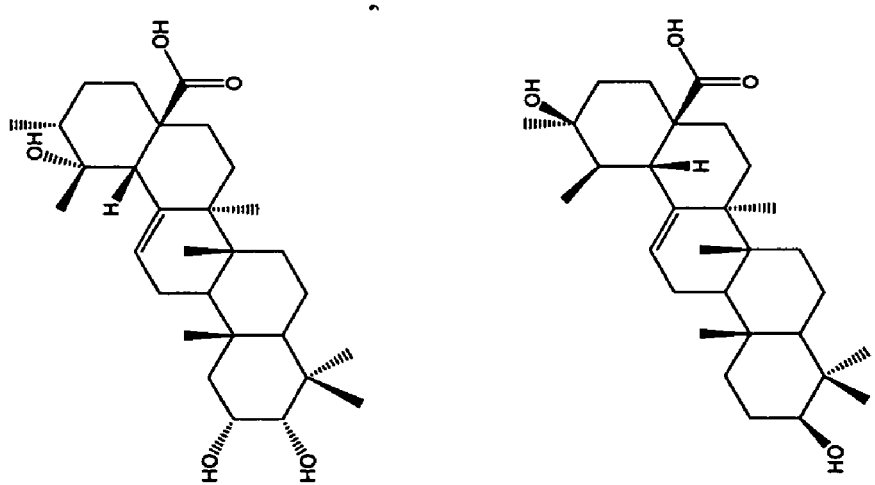
Figure 7:
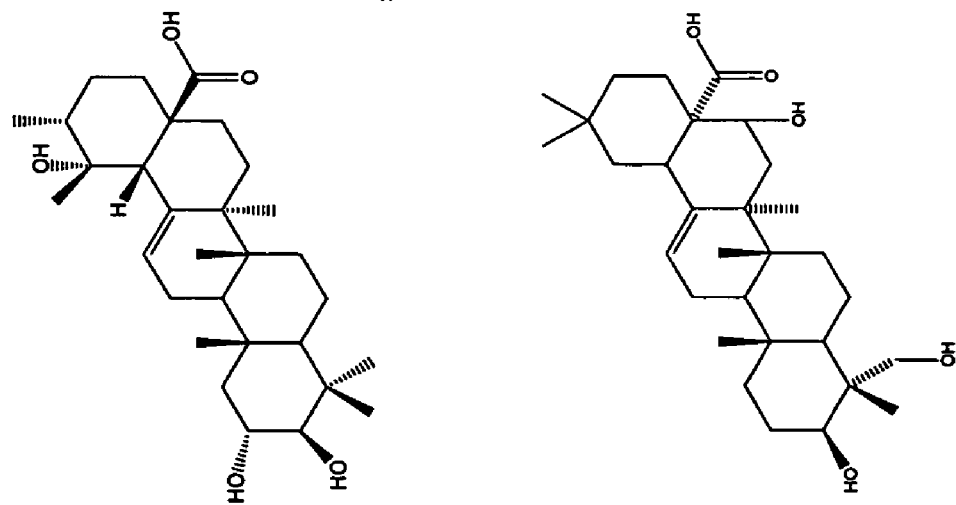
Figure 8:
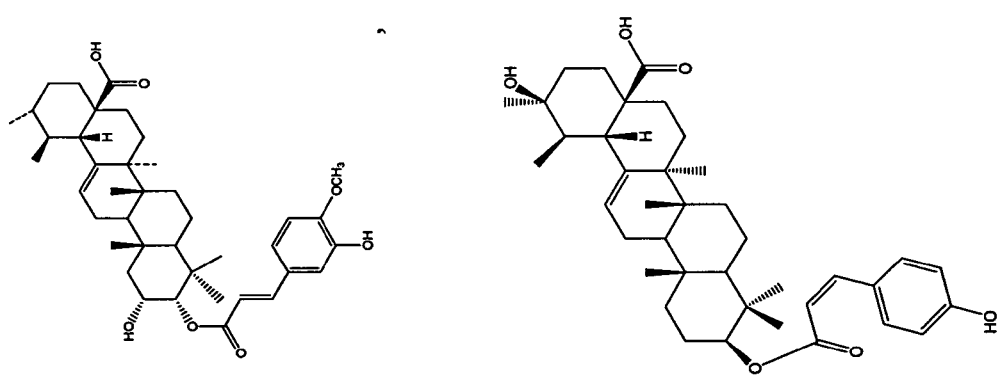

Effect of adding 30 µg/mL ursolic acid on biofilm formation in LB medium in the presence the cysB mutation (E. coli K12[R1drd19] vs. E. coli K12 cysB[R1drd19], data collected 16 hours after addition of ursolic acid. All biofilm mass readings at OD540 were normalized based on the reading of wild type without ursolic acid which was normalized to 1. One standard deviation shown. The results are shown in FIG. 3.

Example 5

Example 1 was repeated, except asiatic acid was added with inoculation in E. coli JM109 in MC9 glucose media.

Asiatic acid demonstrated approximately 75%, 80%, and 85% biofilm inhibition when tested at 5 µg/ml, 10 µg/ml, and 15 µg/ml, respectively.

Example 6

Example 3 was repeated, except asiatic acid (C255) was added instead of ursolic acid. The results are shown in Table 2.

TABLE 2

E. coli JM109 genes induced by 10 µg/ml and 30 µg/ml asiatic acid in M9C glucose media. The underlying ratios indicate the corresponding genes were significantly induced by asiatic acid. ER is expression ratio and Pv is p-value.

| Gene | b# | 10 µg/mL Asiatic Acid | | 30 µg/mL Asiatic Acid | | Description |
|---|---|---|---|---|---|---|
| | | ER | Pv | ER | Pv | |
| b0829 | b0829 | 0.000001 | 2.83 | 0.000001 | 2.46 | putative ATP-binding component of a transport system |
| b1729 | b1729 | 0.000001 | 2.64 | 0.000001 | 2.30 | part of a kinase |
| b1963 | b1963 | 0.000838 | 2.14 | 0.000007 | 2.30 | orf, hypothetical protein |
| b2332 | b2332 | 0.000002 | 2.14 | 0.000002 | 2.30 | orf, hypothetical protein |
| b2420 | b2420 | 0.000006 | 4.29 | 0.004108 | 2.14 | orf, hypothetical protein |
| b2531 | b2531 | 0.000002 | 2.46 | 0.000002 | 2.14 | orf, hypothetical protein |
| b2670 | b2670 | 0.000001 | 3.25 | 0.002057 | 2.64 | orf, hypothetical protein |
| b2834 | b2834 | 0.000063 | 2.30 | 0.000121 | 2.00 | orf, hypothetical protein |
| bolA | b0435 | 0.000001 | 2.30 | 0.000001 | 2.64 | possible regulator of murein genes |
| cbl | b1987 | 0.000001 | 13.93 | 0.000001 | 13.00 | transcriptional regulator cys regulon; accessory regulatory circuit affecting cysM |
| cysA | b2422 | 0.000002 | 4.00 | 0.000002 | 3.48 | ATP-binding component of sulfate permease A protein; chromate resistance |
| cysB | b1275 | 0.000001 | 6.06 | 0.000001 | 4.29 | positive transcriptional regulator for cysteine regulon |
| cysC | b2750 | 0.000001 | 10.56 | 0.000001 | 6.96 | adenosine 5-phosphosulfate kinase |
| cysD | b2752 | 0.000001 | 6.96 | 0.000001 | 6.50 | ATP:sulfurylase (ATP:sulfate adenylyltransferase), subunit 2 |
| cysH | b2762 | 0.000001 | 4.59 | 0.000001 | 3.03 | 3-phosphoadenosine 5-phosphosulfate reductase |
| cysI | b2763 | 0.000002 | 4.29 | 0.000002 | 3.25 | sulfite reductase, alpha subunit |
| cysJ | b2764 | 0.000002 | 3.73 | 0.000002 | 4.00 | sulfite reductase (NADPH), flavoprotein beta subunit |
| cysK | b2414 | 0.000001 | 4.59 | 0.000001 | 3.48 | cysteine synthase A, O-acetylserine sulfhydrolase A |
| cysM | b2421 | 0.000001 | 3.73 | 0.000004 | 3.25 | cysteine synthase B, O-acetylserine sulfhydrolase B |
| cysN | b2751 | 0.000001 | 11.31 | 0.000001 | 7.46 | ATP-sulfurylase (ATP:sulfate adenylyltransferase), subunit 1, probably a GTPase |

TABLE 2-continued

E. coli JM109 genes induced by 10 µg/ml and 30 µg/ml asiatic acid in M9C glucose media. The underlying ratios indicate the corresponding genes were significantly induced by asiatic acid. ER is expression ratio and Pv is p-value.

| Gene | b# | 10 µg/mL Asiatic Acid | | 30 µg/mL Asiatic Acid | | Description |
| --- | --- | --- | --- | --- | --- | --- |
| | | ER | Pv | ER | Pv | |
| cysP | b2425 | 0.000001 | 4.29 | 0.000001 | 4.92 | thiosulfate binding protein |
| cysU | b2424 | 0.000002 | 4.92 | 0.000002 | 4.92 | sulfate, thiosulfate transport system permease T protein |
| cysW | b2423 | 0.000002 | 4.59 | 0.000002 | 4.00 | sulfate transport system permease W protein |
| dgt | b0160 | 0.000002 | 2.14 | 0.000057 | 2.30 | deoxyguanosine triphosphate triphosphohydrolase |
| fliY | bi920 | 0.000002 | 4.00 | 0.000002 | 3.25 | putative periplasmic binding transport protein |
| ftn | b1905 | 0.000001 | 3.25 | 0.000001 | 3.03 | cytoplasmic ferritin (an iron storage protein) |
| glgS | b3049 | 0.000001 | 2.14 | 0.000001 | 2.30 | glycogen biosynthesis, rpoS dependent |
| ilvG_1 | b3767 | 0.000005 | 2.83 | 0.000059 | 2.00 | acetolactate synthase II, large subunit, cryptic, interrupted |
| ilvL | b3766 | 0.000003 | 2.30 | 0.000005 | 3.48 | ilvGEDA operon leader peptide |
| msrA | b4219 | 0.000001 | 2.30 | 0.000001 | 2.64 | peptide methionine sulfoxide reductase |
| nlpA | b3661 | 0.000001 | 18.38 | 0.000001 | 9.85 | lipoprotein-28 |
| pssR | b3763 | 0.001336 | 2.46 | 0.001832 | 2.14 | regulator of pssA |
| pstS | b3728 | 0.000002 | 2.64 | 0.000002 | 2.00 | high-affinity phosphate-specific transport system; periplasmic phosphate-binding protein |
| sbp | b3917 | 0.000001 | 18.38 | 0.000001 | 12.13 | periplasmic sulfate-binding protein |
| tauA | b3065 | 0.000001 | 2.46 | 0.000001 | 2.00 | taurine transport system periplasmic protein |
| yaeG | b0162 | 0.007398 | 4.59 | 0.042948 | 4.00 | orf, hypothetical protein |
| yaiB | b0382 | 0.000001 | 2.30 | 0.000014 | 2.64 | orf, hypothetical protein |
| ybgR | b0752 | 0.000002 | 2.46 | 0.000002 | 2.46 | putative transport system permease protein |
| ybiK | b0828 | 0.000001 | 6.50 | 0.000001 | 5.66 | putative asparaginase |
| yciW | b1287 | 0.000002 | 3.03 | 0.000002 | 3.73 | putative oxidoreductase |
| yedO | b1919 | 0.000002 | 3.73 | 0.000002 | 2.83 | putative 1-aminocyclopropane-1-carboxylate deaminase |
| yeeD | b2012 | 0.000002 | 3.73 | 0.000002 | 2.30 | orf, hypothetical protein |
| yeeE | b2013 | 0.000002 | 3.25 | 0.000002 | 2.14 | putative transport system permease protein |
| ygbE | b2749 | 0.000002 | 6.96 | 0.000004 | 5.28 | putative cytochrome oxidase subunit |
| yicG | b3646 | 0.000001 | 2.83 | 0.000001 | 2.30 | orf, hypothetical protein |
| yicL | b3660 | 0.000001 | 6.50 | 0.000057 | 2.83 | putative permease transporter |
| yjaE | b3995 | 0.000002 | 2.00 | 0.000002 | 2.14 | putative transcriptional regulator |
| yjiD | b4326 | 0.000001 | 7.46 | 0.000001 | 9.85 | orf, hypothetical protein |
| yrbL | b3207 | 0.000001 | 2.64 | 0.000001 | 2.46 | orf, hypothetical protein |

What is claimed:

1. A method for reducing or inhibiting a biofilm comprising modulating expression of a cysB gene present in a Gram-negative bacteria cell capable of biofilm formation, thereby to reduce or inhibit the biofilm formation.

2. The method of claim 1, wherein modulation of the cysB gene comprises contacting the cell with a composition comprising a compound selected from the group consisting of ursolic acid or asiatic acid, or a pharmaceutically acceptable salt of such compound, a hydrate of such compound, a solvate of such compound, an N-oxide of such compound, or a combination thereof.

3. The method of claim 2, wherein the compound is ursolic acid.

4. The method of claim 2, wherein the compound is asiatic acid.

5. The method of claim 1, wherein the cell is selected from a group consisting of Escherichia coli, Proteus mirablis, Francisella tularensis, Vibrio sp., Pseudomonas aeruginosa, V. harveyi, Pseudomonas sp., Salmonella sp., Haemophilus influenzae, Neisseria sp., Burkholderia sp., Klebsiella sp., and Yersinia pestis.

6. The method of claim 5, wherein the cell is Escherichia coli.

7. The method of claim 5, wherein the cell is Pseudomonas aeruginosa.

8. The method of claim 5, wherein the cell is V. harveyi.

9. A method for modulating the expression of cysB, comprising contacting a Gram-negative bacteria cell capable of biofilm formation with a composition comprising a compound selected from the group consisting of ursolic acid or asiatic acid, or a pharmaceutically acceptable salt of such compound, a hydrate of such compound, a solvate of such compound, a N-oxide of such compound, or a combination thereof.

10. The method of claim 9, wherein the compound is ursolic acid.

11. The method of claim 9, wherein the compound is asiatic acid.

12. The method of claim 9, wherein the cell is selected from a group consisting of Escherichia coli, Proteus mirablis, Francisella tularensis, Vibrio sp., Pseudomonas aeruginosa, V. harveyi, Pseudomonas sp., Salmonella sp., Haemophilus influenzae, Neisseria sp., Burkholderia sp., Klebsiella sp., and Yersinia pestis.

13. The method of claim 12, wherein the cell is Escherichia coli.

14. The method of claim 12, wherein the cell is Pseudomonas aeruginosa.

15. The method of claim 12, wherein the cell is V. harveyi.

* * * * *